United States Patent
Murata et al.

(10) Patent No.: US 10,746,647 B2
(45) Date of Patent: Aug. 18, 2020

(54) ANALYSIS DEVICE, ANALYSIS METHOD, ANALYSIS PROGRAM, CELL MANUFACTURING METHOD AND CELLS

(71) Applicants: THE UNIVERSITY OF TOKYO, Tokyo (JP); NIKON CORPORATION, Tokyo (JP)

(72) Inventors: Masayuki Murata, Tokyo (JP); Fumi Kano, Tokyo (JP); Yoshiyuki Noguchi, Tokyo (JP); Nobuhiko Maiya, Yokohama (JP); Chisako Iwamoto, Yokohama (JP); Shoko Yamasaki, Tokyo (JP); Masafumi Yamashita, Fujisawa (JP)

(73) Assignees: THE UNIVERSITY OF TOKYO, Tokyo (JP); NIKON CORPORATION, Tokyo (JP)

( * ) Notice: Subject to any disclaimer, the term of this patent is extended or adjusted under 35 U.S.C. 154(b) by 0 days.

(21) Appl. No.: 15/630,543

(22) Filed: Jun. 22, 2017

(65) Prior Publication Data
US 2017/0350805 A1   Dec. 7, 2017

Related U.S. Application Data

(63) Continuation of application No. PCT/JP2014/084664, filed on Dec. 26, 2014.

(51) Int. Cl.
*G06T 9/00* (2006.01)
*G01N 15/14* (2006.01)
(Continued)

(52) U.S. Cl.
CPC .......... *G01N 15/1475* (2013.01); *C12M 1/34* (2013.01); *G01N 21/27* (2013.01); *G01N 33/48* (2013.01);
(Continued)

(58) Field of Classification Search
None
See application file for complete search history.

(56) References Cited

U.S. PATENT DOCUMENTS

| 9,280,698 | B2 | 3/2016 | Kii et al. |
| 2005/0014217 | A1 | 1/2005 | Mattheakis et al. |

(Continued)

FOREIGN PATENT DOCUMENTS

| GB | 2435926 A | 9/2007 |
| JP | 2011-239778 A | 12/2011 |

(Continued)

OTHER PUBLICATIONS

Mar. 31, 2015 Search Report issued in International Patent Application No. PCT/JP2014/084664.
(Continued)

*Primary Examiner* — Sean M Conner
(74) *Attorney, Agent, or Firm* — Oliff PLC

(57) ABSTRACT

An analysis device includes an acquisition unit configured to acquire an image of a cell and an identification unit configured to identify elements that are identifiable on the basis of the image of cell acquired by the acquisition unit. Characteristic quantities of the elements identified by the identification unit are calculated, a correlation between the characteristic quantities is calculated on the basis of the calculated characteristic quantities of the elements, and a correlation between the elements is calculated on the basis of the calculated correlation between the characteristic quantities.

32 Claims, 34 Drawing Sheets

(51) Int. Cl.
  *C12M 1/34* (2006.01)
  *G06T 7/20* (2017.01)
  *G01N 33/483* (2006.01)
  *G01N 33/48* (2006.01)
  *G01N 21/27* (2006.01)
  *G06T 7/00* (2017.01)
  *G01N 15/00* (2006.01)
  *G01N 15/10* (2006.01)

(52) U.S. Cl.
  CPC ......... *G01N 33/483* (2013.01); *G06T 7/0012* (2013.01); *G06T 7/20* (2013.01); *G01N 2015/0065* (2013.01); *G01N 2015/1006* (2013.01); *G01N 2015/1497* (2013.01); *G06T 2207/10056* (2013.01); *G06T 2207/30024* (2013.01)

(56) References Cited

U.S. PATENT DOCUMENTS

| | | | | |
|---|---|---|---|---|
| 2006/0280352 A1* | 12/2006 | Muschler | ............. | G06K 9/0014 382/133 |
| 2010/0311101 A1* | 12/2010 | Compagnone | ..... | G01N 33/5076 435/29 |
| 2011/0228069 A1* | 9/2011 | Mimura | ................ | C12M 23/48 348/79 |
| 2012/0069170 A1* | 3/2012 | Gesley | ............... | G01N 21/6458 348/79 |
| 2012/0092478 A1* | 4/2012 | Honda | .................. | C12M 41/14 348/79 |
| 2014/0120550 A1* | 5/2014 | Baranov | ................ | G01N 15/10 435/7.1 |
| 2014/0134635 A1* | 5/2014 | Jiang | .................... | C12Q 1/6886 435/6.13 |
| 2014/0193052 A1* | 7/2014 | Yoshihara | ............. | G06F 19/321 382/128 |
| 2014/0247972 A1* | 9/2014 | Wang | ................... | G06K 9/6227 382/133 |
| 2014/0294279 A1* | 10/2014 | Madabhushi | ......... | G06T 7/0014 382/133 |
| 2015/0080233 A1* | 3/2015 | Bendall | .............. | G01N 33/5005 506/4 |
| 2015/0213614 A1* | 7/2015 | Maddah | .................. | G06T 7/246 382/133 |
| 2015/0310254 A1* | 10/2015 | Chennubhotla | ......... | G06T 7/262 382/133 |
| 2017/0091937 A1* | 3/2017 | Barnes | ................. | C12Q 1/6886 |
| 2017/0166858 A1 | 6/2017 | Honda et al. | | |

FOREIGN PATENT DOCUMENTS

| | | |
|---|---|---|
| WO | 02/066961 A1 | 8/2002 |
| WO | 2007/028944 A1 | 3/2007 |
| WO | 2010/098105 A1 | 9/2010 |

OTHER PUBLICATIONS

Mar. 31, 2015 Written Opinion issued in International Patent Application No. PCT/JP2014/084664.
Jul. 17, 2018 Extended Search Report issued in European Patent Application No. 14909103.5.
Aug. 28, 2018 Office Action issued in Japanese Application No. 2016-565839.
May 7, 2019 Notice of Reasons for Rejection issued in Japanese Patent Application No. 2016-565839.

* cited by examiner

| MAIN | SECONDARY |
|---|---|
| a | b, c, d, f |
| d | b, c, f |
| b | c, f |
| f | c |
| a&d | b, c, f |
| a&b | c, f |
| a&f | c |
| a&d&b | c, f |
| a&d&f | c |
| a&b&f | c |
| d&b | c, f |
| d&f | c |
| b&f | c |

FIG. 18

| MAIN | SECONDARY |
|------|-----------|
| a | b, f |
| d | c |
| b | f |
|  |  |
| a&d | b, f |
| a&b | f |
|  |  |
| a&d&b | f |
|  |  |
|  |  |
| d&b | c, f |
|  |  |
|  |  |

FIG. 20

| MAIN | SECONDARY |
|------|-----------|
| a | f |
| d | c |
|  |  |
|  |  |
| a&d | b |
|  |  |
|  |  |
|  |  |
|  |  |
| d&b | c |
|  |  |
|  |  |

FIG. 22

| CELL ID | a→b | a→f | b→g | d→b | d→c | ... | n |
|---|---|---|---|---|---|---|---|
| 1 | 0.85 | −0.68 | 0.70 | 0.92 | −0.88 | ... | ... |
| 2 | 0.79 | −0.81 | 0.55 | 0.95 | −0.74 | ... | ... |
| 3 | 0.36 | −0.24 | 0.68 | 0.41 | −0.86 | ... | ... |
| ⋮ | ⋮ | ⋮ | ⋮ | ⋮ | ⋮ | ... | ... |

FIG. 27

ANALYSIS DEVICE, ANALYSIS METHOD, ANALYSIS PROGRAM, CELL MANUFACTURING METHOD AND CELLS

CROSS-REFERENCE TO RELATED APPLICATION

This is a Continuation Application of International Application No. PCT/JP2014/84664, filed Dec. 26, 2014. The contents of which are hereby incorporated by reference in their entirety.

BACKGROUND

Field of the Invention

The present invention relates to an analysis device, an analysis method, an analysis program, a cell manufacturing method, and cells.

Description of Related Art

In biological science, medical science and the like, it is known that there is a correlation, for example, between a state of health, disease or the like and a state of cells, organelles inside the cells and the like. Thus, analyzing the correlation between these is one technique for solving various issues in biological science, medical science and the like. Further, for example, analyzing transduction pathways of information transmitted between cells or within cells can be helpful for research relating to biosensors in industrial applications, in the manufacture of drugs with the aim of preventing disease, and the like.

In various analysis techniques relating to cells and tissue slices, techniques using image processing are known, for example U.S. Pat. No. 9,280,698. These conventional techniques, for example, are techniques in which image processing is performed on images of cells acquired from a living organism and the like. In these techniques, correlations and differences between characteristic quantities of cell morphologies are calculated by comparing image data of the cells acquired at a predetermined interval with image data relating to the morphology of the cells acquired at a different timing to the acquired image data. In this way, activity of the acquired cells can be determined, and this can be helpful in the elucidation of biological phenomena, such as the development of cancer, disease or the like of the cells.

SUMMARY

Summary of Invention

Technical Problem

However, in the above-described conventional techniques, since the correlations and differences between the characteristic quantities are solely calculated from the information acquired by the image processing on the images related to the morphology of the cells, the acquired information is sometimes insufficient.

In this way, in the above-described conventional techniques, it is sometimes difficult to analyze relationships between elements configuring mechanisms that control vital phenomena relating to cells.

Taking this type of situation into account, it is an object of the present invention to provide an analysis device, an analysis method, an analysis program, a cell manufacturing method, and cells capable of appropriately analyzing images while also being capable of analyzing relationships between elements configuring mechanisms that control vital phenomena relating to cells.

Solution to Problem (1) An aspect of the present invention is an analysis device including: an acquisition unit configured to acquire an image of a cell; an identification unit configured to identify elements that are identifiable on the basis of the image of the cell acquired by the acquisition unit; and a calculation unit configured to calculate characteristic quantities of the elements for each of the elements identified by the identification unit, to calculate a correlation between the characteristic quantities on the basis of the characteristic quantities of the elements that are calculated, and to calculate a correlation between the elements on the basis of the correlation that is calculated between the characteristic quantities.

(2) Another aspect of the present invention is an analysis method including the steps of: causing an analysis device, which acquires an image of a cell, identifies elements that are identifiable on the basis of the image of the cell that is acquired, calculates characteristic quantities of the elements for each of the elements that are identified, calculates a correlation between the characteristic quantities on the basis of the characteristic quantities of the elements that are calculated, and calculates a correlation between the elements on the basis of the correlation that is calculated between the characteristic quantities, to perform analysis of the image of the cell that is acquired, and causing the analysis device to newly acquire the image of the cell and repeatedly perform the analysis until a model representing a correlation between elements calculated by the analysis device becomes a predetermined relationship.

(3) Another aspect of the present invention is an analysis program causing execution of steps including: processing causing an analysis device, which acquires an image of a cell, identifies elements that are identifiable on the basis of the image of the cell that is acquired, calculates characteristic quantities of the elements for each of the elements that are identified, calculates a correlation between the characteristic quantities on the basis of the characteristic quantities of the elements that are calculated, and calculates a correlation between the elements on the basis of the correlation that is calculated between the characteristic quantities, to perform analysis of the image of the cell that is acquired; and processing causing the analysis device to newly acquire the image of the cell and repeatedly perform the analysis until a model representing a correlation between elements calculated by the analysis device becomes a predetermined relationship.

(4) Another aspect of the present invention is a cell manufacturing method including the steps of: causing an analysis device, which acquires an image of a cell, identifies elements that are identifiable on the basis of the image of the cell that is acquired, calculates characteristic quantities of the elements for each of the elements that are identified, calculates a correlation between the characteristic quantities on the basis of the characteristic quantities of the elements that are calculated, and calculates a correlation between the elements on the basis of the correlation that is calculated between the characteristic quantities, to perform analysis of the image of the cell that is acquired; and causing the analysis device to newly acquire the image of the cell and repeatedly perform the analysis until a model representing a correlation between elements calculated by the analysis device becomes a predetermined relationship.

(5) Another aspect of the present invention is a cell manufactured using the above-described cell manufacturing method.

According to the present invention, relationships between elements configuring mechanisms that control vital phenomena relating to cells can be analyzed while appropriately analyzing images.

BRIEF DESCRIPTION OF THE DRAWINGS

FIG. 17 is a diagram illustrating an example of characteristic data indicating a strong correlation with respect to characteristic data a.

FIG. 18 is a diagram illustrating an example of a correspondence table of correlations between all of the characteristic data constructed by a mechanism analysis unit 124.

FIG. 20 is a diagram illustrating an example of a correspondence table of correlations between characteristic data newly calculated by the mechanism analysis unit 124.

FIG. 22 is a diagram illustrating another example of a correspondence table of correlations between characteristic data newly calculated by the mechanism analysis unit 124.

FIG. 27 is a diagram illustrating an example of cross correlation coefficients calculated by the mechanism analysis unit 124.

DESCRIPTION OF EMBODIMENTS

An embodiment of an observation device according to the present invention will be described below with reference to the drawings. In the following embodiment, processing will be described in which, to elucidate vital phenomena, a model of a signaling cascade of a protein, which is an element configuring a mechanism that controls vital phenomena, is constructed and analyzed, for example. The signaling cascade is an example of a mechanism showing transduction pathways of signals when a signal is created by a stimulus applied to a cell first or a change in the state of the cell itself, and the signals are then transmitted in a chain between elements configuring the cell, such signals sequentially increasing, reducing, or performing feedback control of the elements affected at the time of signal transduction.

Figure 1:
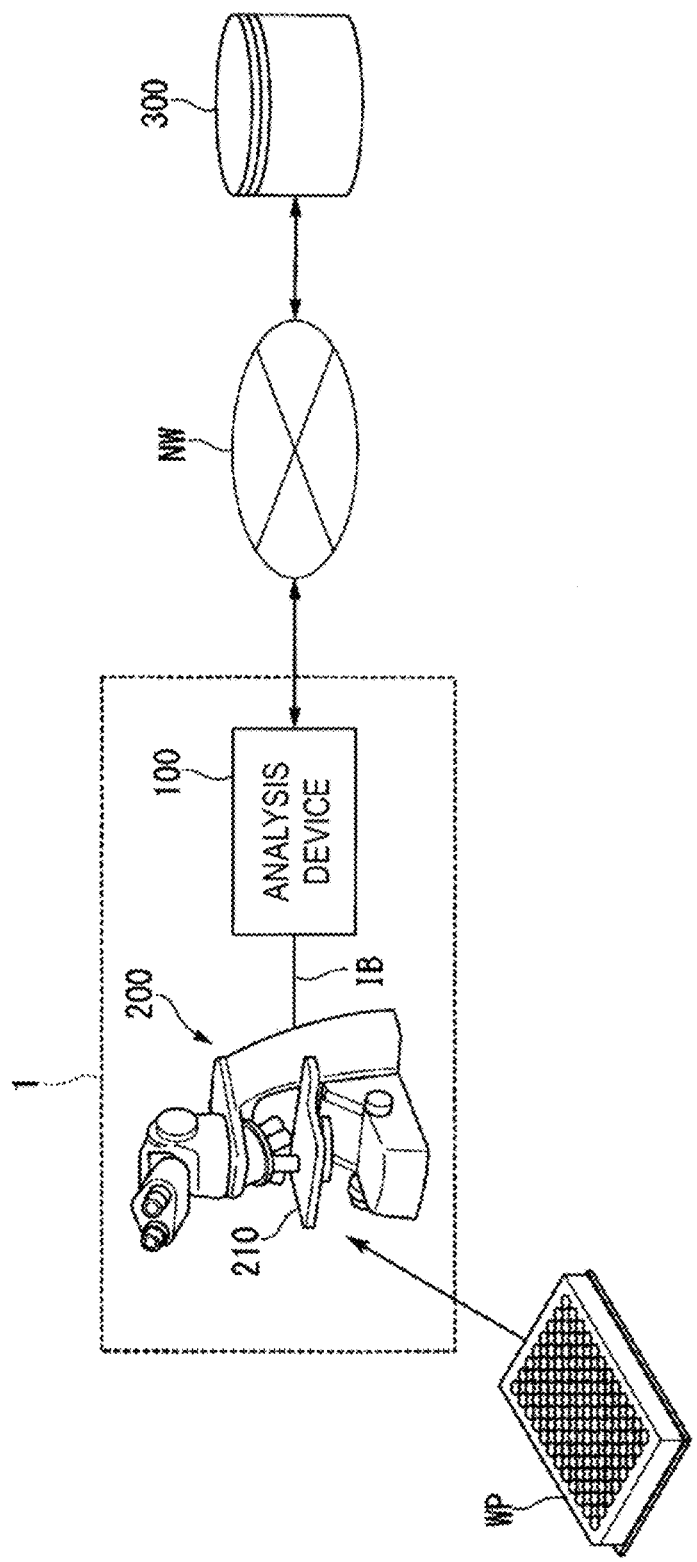
FIG. 1 is a diagram schematically illustrating an example of a configuration of an observation device 1 including an analysis device 100 according to an embodiment.

Below, an embodiment of an analysis device 100 according to an embodiment of the present invention will be described. FIG. 1 is a diagram schematically illustrating an example of a configuration of an observation device 1 including the analysis device 100 according to an embodiment.

The observation device 1 is, for example, a device that analyzes images acquired by image capture of cells or the like. In the observation device 1, for example, the analysis device 100 connected to a microscope 200 via an internal bus IB communicates with an external storage device 300 or the like over a network NW. The network NW is a communication line, such as the Internet or a telephone line.

The microscope 200 is, for example, a biological microscope provided with an electromotive stage 210 that can move as desired, in a two-dimensional plane in a horizontal direction, a position of an image capture target (a culture vessel, for example). The microscope 200 has, for example, functions such as a differential interference contrast microscope (Differential Interference Contrast microscope; DIC), a phase contrast microscope, a fluorescence microscope, a confocal microscope, or a super-resolution microscope. The microscope 200 captures images of the culture vessel (a well plate WP, for example) placed on the electromotive stage 210. The microscope 200 irradiates cells cultivated inside a plurality of wells (holes) provided in the well plate WP with light, and thus performs image capture of the transmitted light transmitted through the cells, as the image of the cells. In this way, an image of the cells can be obtained, such as a transmission DIC image, a phase contrast image, a dark field image, and a bright field image. In addition, by irradiating the cells with excitation light that excites fluorescent material, an image can be captured of fluorescence emitted from the fluorescent material, as the image of the cells. Alternatively, the microscope 200 may capture, as the above-described image of the cells, an image of fluorescence emitted from the fluorescent material itself incorporated in biological material, or of fluorescence emitted by a material having chromophores being combined with the biological material. In this way, the observation device 1 can acquire a fluorescence image, a confocal image, and a super-resolution image. The cells of the present embodiment are, for example, primary cultured cells, subculture cells, tissue sections and the like. Note that the state of the cells is not particularly limited to a specific state, and they may be in a living state or may be in a fixed state. Specifically, they may be one of either "in-vivo" or "in-vitro."

Figure 2:
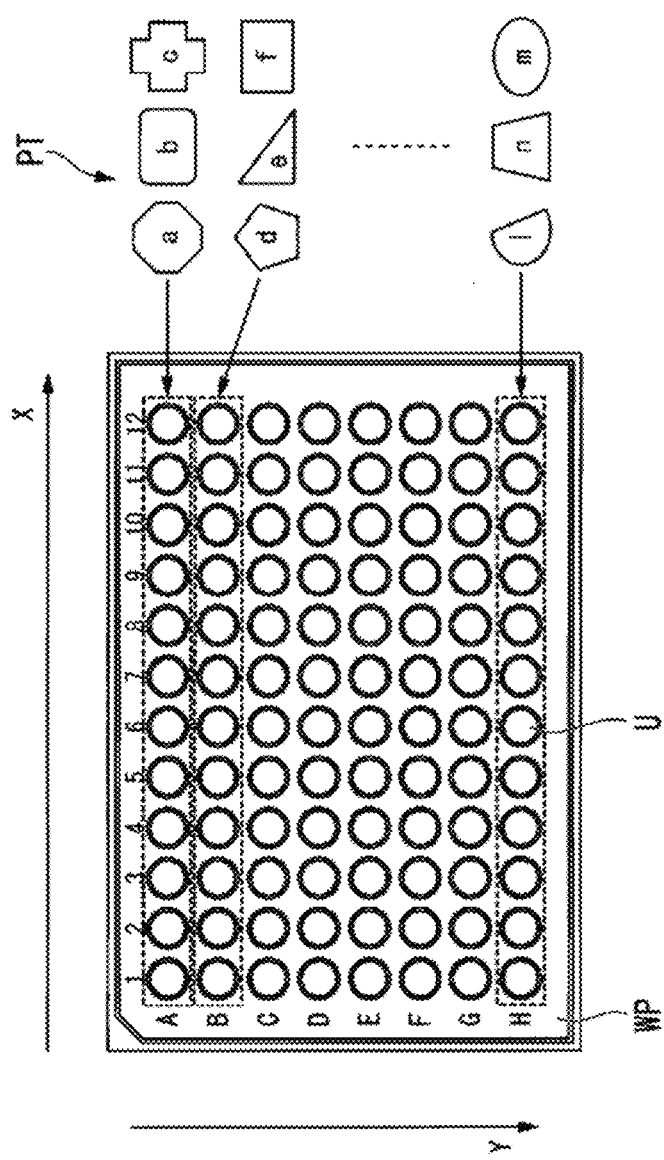
FIG. 2 is a diagram illustrating an example of cells and elements thereof cultivated on a well plate WP.

FIG. 2 is a diagram illustrating an example of cells and elements thereof cultivated on the well plate WP. The well plate WP is, for example, a plate having 96 (12×8) wells U for cultivating cells. The cells cultivated in the wells U are cultivated under specific conditions. The specific conditions include an elapsed time period from when the stimulus is applied, a type and strength of the applied stimulus, a presence or absence of the stimulus, induction of biological characteristics, and the like. The stimulus is, for example, a physical stimulus such as electricity, sound waves, magnetism, or light, or a chemical stimulus obtained by administering a substance, a drug or the like. Further, the biological characteristics are characteristics indicating a stage of differentiation of the cells, a morphology, the number of the cells and the like.

The cells are, for example, cultivated while being sorted into 12 stages depending on the type of specific conditions, on the well plate WP in the longitudinal direction (a direction X). In addition, the cells sorted into the 12 stages are sorted by each of analysis targets on the well plate WP in the lateral direction (a direction Y). The analysis targets are elements configuring mechanisms that control the vital phenomena, and include the cell, the nucleus of the cell, small cellular organs (organelles) such as structures inside the nucleus, mitochondria, and endoplasmic reticulum, cell matrices, and biological materials such as cell surface carbohydrate chains, intracellular proteins, peptides, mRNA (nucleic acid), metabolites, reactive oxygen species, and various ions.

As illustrated in FIG. 2, the elements that are the analysis targets are sorted, for example, into respective groups of three types, as follows: elements a to c in a first row (row A) of the plate, elements d to f in a second row (row B), and continuing in this manner to elements l to m in an eighth row (row H). Note that the well plate WP is not limited to having the 96 wells U, and may be a plate having any number of wells U. In accordance with this, the cells may also be sorted into any number of stages. Further, the culture vessel is not limited to the well plate WP, and as long as the image can be captured by the microscope 200, any type of plate may be used, and may be a petri dish, a slide glass or the like, for example.

Alternatively, the image may be indirectly captured by dyeing or labeling the analysis targets using a fluorescent material or the like. Further, the elements configuring the mechanisms that control the vital phenomena are not limited only to those elements configuring the innate mechanisms of the cell itself, and may be an element artificially added to the innate mechanisms of the cell itself, such as an inhibitor, an agonist, or a virus.

Figure 3:
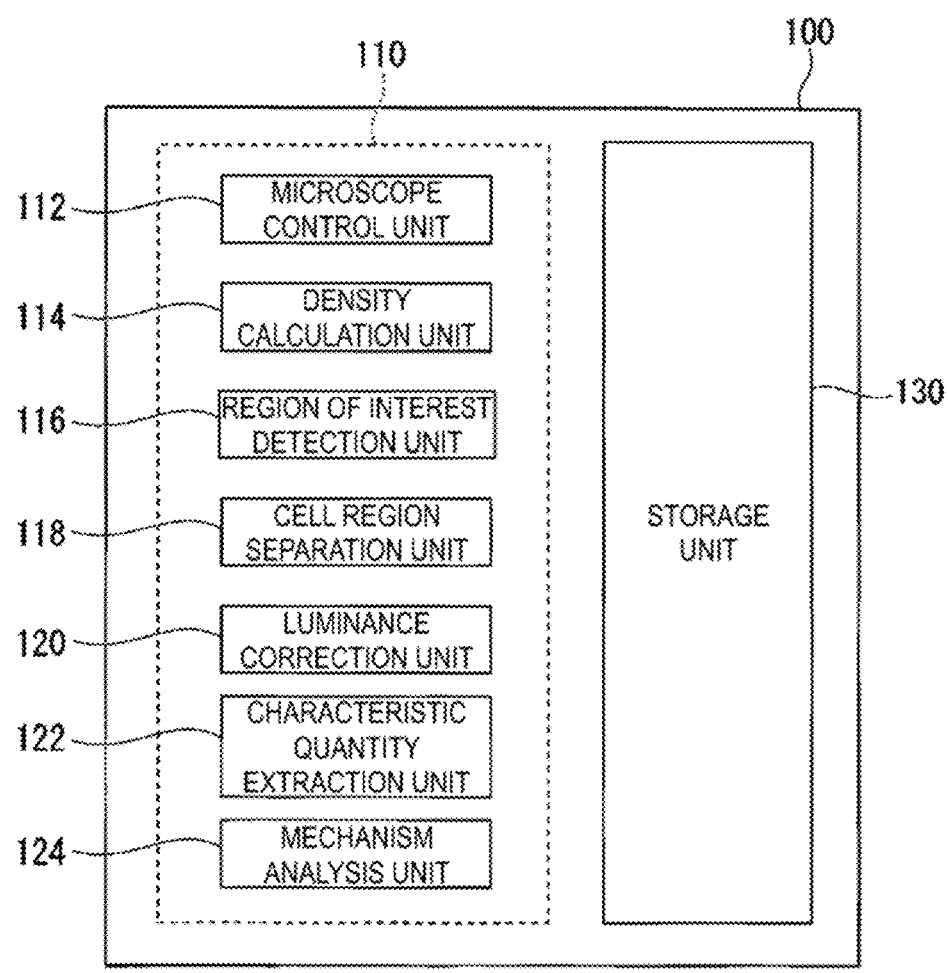
FIG. 3 is a schematic diagram illustrating an example of a function configuration of the analysis device 100.

FIG. 3 is a schematic diagram illustrating an example of a function configuration of the analysis device 100. The analysis device 100 is a computer device that analyzes the image obtained by the microscope 200. Note that the images to be analyzed by the analysis device 100 are not limited to the images captured by the microscope 200, and may be, for example, images stored in advance in a storage unit 130 inside the analysis device 100, or may be images stored in advance in the external storage device 300.

The analysis device 100 is provided with a processor such as a central processing unit (CPU), the storage unit 30 such as a Read Only Memory (ROM) or a Random Access Memory (RAM), a Hard Disk Drive (HDD), an Electrically Erasable Programmable Read-Only Memory (EEPROM), and a flash memory, and a communication interface and the like for communicating with other devices.

The analysis device 100 is provided with a control unit 110 and the storage unit 130. The control unit 110 is provided with a microscope control unit 112, a density calculation unit 114, a region of interest detection unit 116, a cell region separation unit 118, a luminance correction unit 120, a characteristic quantity extraction unit 122, and a mechanism analysis unit 124. The control unit 110 is configured, for example, by software functional portions that function by a program stored in the storage unit 130 being executed by the processor. Further, some or all of each of these functional portions of the control unit 110 may be configured by a hardware functional portion, such as Large Scale Integration (LSI) or an Application Specific Integrated Circuit (ASIC).

The storage unit 130 is controlled so as to store parameters for experimental conditions used in pre-observation and actual observation, information obtained as a result of processing by the control unit 110, and information and the like relating to cells. Note that the storage unit 130 need not necessarily be incorporated into the analysis device 100, and may be an external storage device (a. Network Attached Storage (NAS) device, for example).

Pre-Observation

Before performing the "actual observation" that will be described hereinafter, the observation device 1 performs the "pre-observation." The pre-observation is processing that is automatically performed in order to derive a region to be observed in the actual observation.

The microscope control unit 112 controls the microscope 200 so as to capture the image of the whole of the culture vessel at a low magnification (wide range). In this way, at the time of image capture, the image can be acquired indicating an area in which the cells suitable to be the analysis target are present, while suppressing phototoxicity or fading of fluorescence occurring as a result of light hitting the cells.

Further, the microscope control unit 112 may control the microscope 200 so as to perform tiling image capture of the whole of the culture vessel at a low to medium magnification. In the tiling image capture, the whole of the culture vessel is divided into two parts, three parts, four parts, or so on and the image capture is performed. In this way, the state of the cells can be observed to a certain extent, and the image can be obtained indicating an area in which the cells suitable to be the analysis target are present. At this time, by performing high speed image capture using a low resolution and a minimum necessary number of fluorescence channels, phototoxicity and decoloration of fluorescence can be suppressed.

Figure 4:
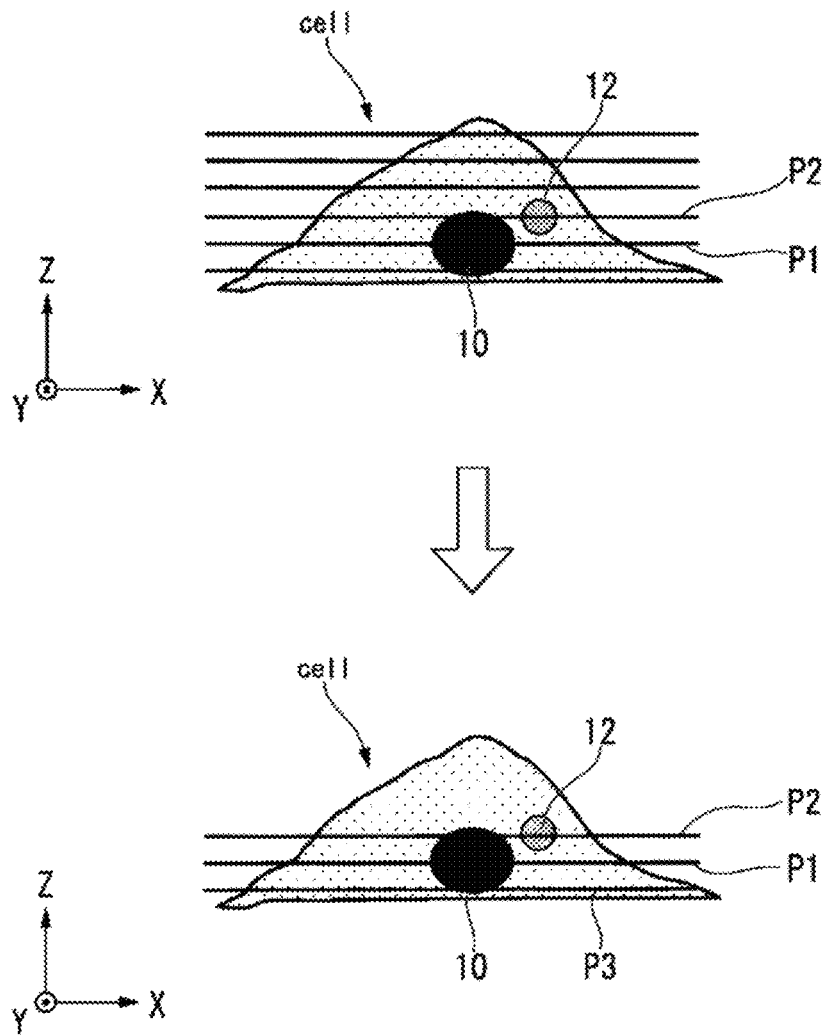
FIG. 4 is cross-sectional views illustrating an example of an interior of a cell "cell."

Further, when the microscope control unit 112 simultaneously performs a plurality of analyses on a single one of the cells "cell," focal position correction data are determined in order to correct the focal position for each of the analysis targets. Here, with reference to FIG. 4, processing performed by the microscope control unit 112 to correct the focal position for each of the analysis targets will be described. FIG. 4 is cross-sectional views illustrating an example of an interior of the cell "cell".

First, the microscope control unit 112 sets, as a best focal position P1, a focal position at which the contrast and integrated value of the luminance values of the whole of the image captured by the microscope 200 are maximum values. Next, the microscope control unit 112 takes the best focal position P1 as a point of origin with respect to the cell "cell," and controls the microscope 200 so as to continuously perform image capture while changing the focal position up and down. In this way, the analysis device 100 can obtain a three-dimensional image of the cell "cell."

The microscope control unit 112 takes the best focal position P1 as a reference, and controls the microscope 200 so as to detect an optimum focal position in accordance with the analysis target. For example, when it is wished to analyze a protein aggregate 12, the microscope control unit 112 sets, as a focal position P2 of the protein aggregate 12, a focal position at which a dispersion value of the luminance values of the whole of the image captured by the microscope 200 is a maximum value, for example. The microscope control unit 112 calculates relative values from the best focal position P1 to the focal position P2 of the protein aggregate 12.

Further, when it is wished to analyze localization changes of a protein inside a cytoplasm, the microscope control unit 112 sets, as a focal position P3, a focal position at which the integrated value of the luminance values of the whole of the image captured by the microscope 200 is a maximum value, for example. Specifically, the microscope control unit 112 sets, as the focal position P3, a position at which an area of the cell "cell" in a plane X-Y is a maximum value. The microscope control unit 112 calculates relative values from the best focal position P1 to the focal position P3.

The microscope control unit 112 stores the various calculated relative values in the storage unit 130, in association with the analysis targets. In this way, when the plurality of analyses are simultaneously performed with respect to the same cell "cell," the optimum focal position can be set by obtaining the relative values associated with each of the analysis targets from the storage unit 130. As a result, the analysis processing can be performed in a shorter time.

Figure 5:
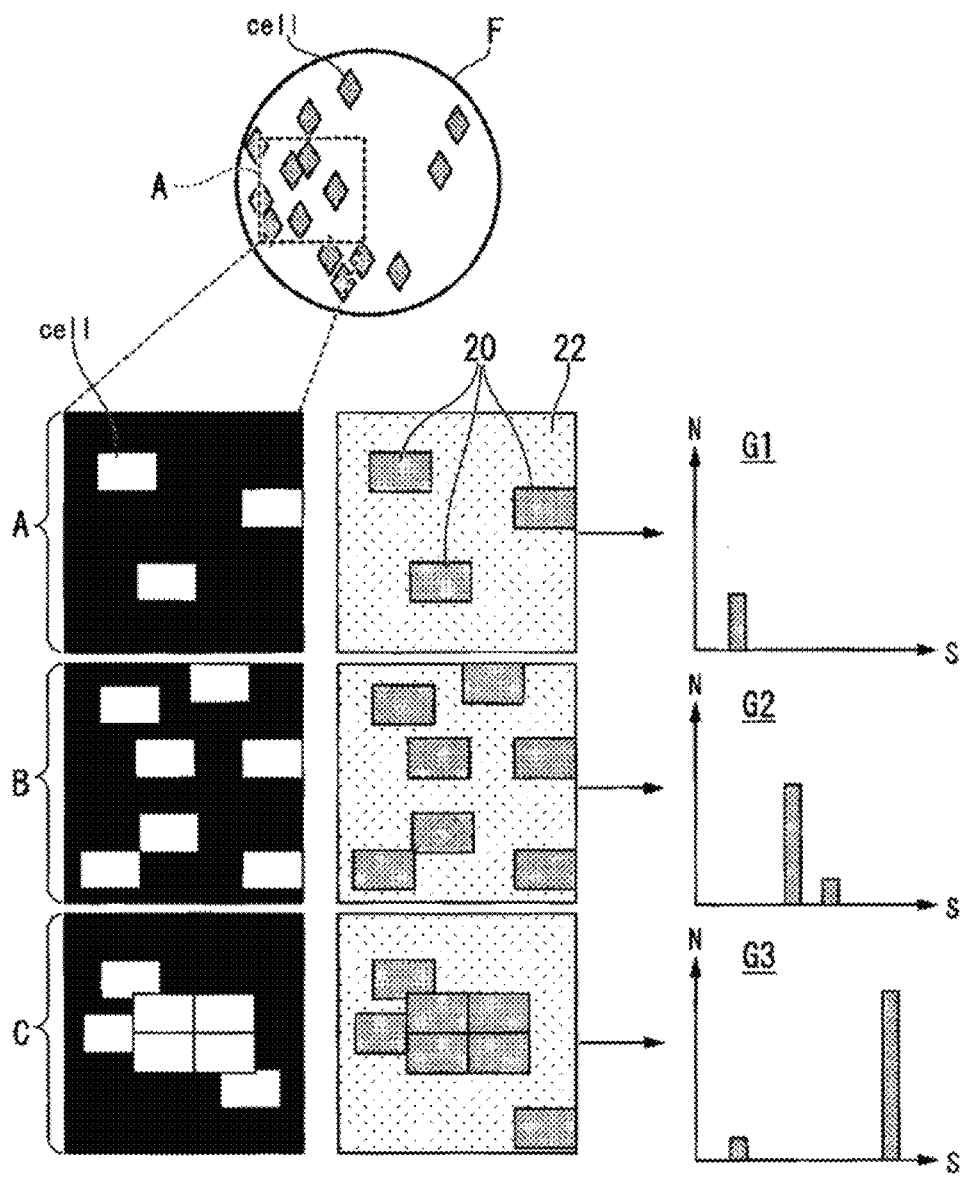
FIG. 5 is a diagram illustrating an example of images when image capture is performed at a low magnification (wide range) of the whole of a culture vessel to which a fluorescent dye reagent has been applied.

FIG. 5 is a diagram illustrating an example of images when image capture is performed at a low magnification (wide range) of the whole of the culture vessel to which a fluorescent dye reagent has been applied.

The density calculation unit 114 calculates a cell density and a degree of cell adhesion of the cells "cell" present in a region F representing the whole image of the culture vessel, in the image obtained by the microscope 200. As illustrated in FIG. 5, the density calculation unit 114 detects, from the images obtained by the microscope 200, regions of the culture vessel in which the cells are present, and extracts freely-selected regions (regions A to C, for example) from those regions. First, the density calculation unit 114 creates a cell region mask, from cell regions 20 representing regions of the cells "cell" present in the freely-selected extracted regions. Then, the density calculation unit 114 creates a background region mask, from a background region 22 representing a region of the region A from which the regions 20 have been subtracted. For example, the density calculation unit 114 creates a cell region mask in which the cell regions 20, which fluoresce at equal to or greater than a predetermined luminance value, are set as "1" and other regions are set as "0," and creates, as the background region mask, a mask excepting the cell regions 20 from the cell region mask. The predetermined luminance value is a luminance value at which it can be determined whether or not the cells are emitting fluorescence or are labeled with fluorescence, and is determined in advance through experimentation or the like.

Next, the density calculation unit 114 calculates a cell density by dividing a total area S of the cell region mask, with respect to the whole region, by a total area of the background region mask. In the case of the region A, for example, since the total area S of the cell region mask is 3 (where the unit is [$\mu m^2$], for example) and the total area of the background region mask is 12 (where the unit is [$\mu m^2$], for example), the density calculation unit 114 calculates the cell density to be 25 (where the unit is [%]).

Further, on the basis of a reference cell size stored in advance in the storage unit 130 and the calculated total area S of the cell region mask, the density calculation unit 114 calculates the number of the cells "cell" present inside the selected regions. For example, by dividing the total area S of the cell region mask by the reference cell size, the density calculation unit 114 calculates the number of the cells "cell." The reference cell size is a value indicating a size per single cell that is statistically calculated in advance in accordance with the cells cultivated in the culture vessel. When the reference cell size is not stored in the storage unit 130, the analysis device 100 may receive, as the reference cell size, a value that is input from an input device (a mouse, a keyboard, or a touch panel, for example), which is not illustrated and is connected to the analysis device 100 via the communication interface. Further, irrespective of whether or not the reference cell size has been stored, the analysis device 100 may overwrite the data stored in the storage unit 130 with the value input from the input device and store the value as the reference cell size.

Further, on the basis of the calculated cell region mask and background region mask, the density calculation unit 114 calculates variations in a distribution of the cells "cell" inside the freely-selected region. When a pixel of the value "1" indicating that the pixel has a luminance value equal to or greater than the predetermined luminance value is configured by a pixel of a size equal to or greater than a predetermined cell size, the density calculation unit 114 calculates the variation in the distribution of the cells "cell" to be a small value. Specifically, when the cells are adjacent to each other or overlap with each other, the density calculation unit 114 calculates a value indicating that variation in the cells inside the freely-selected region are small.

Histograms represented in graphs G1 to G3 of the cells "cell" illustrated in FIG. 5 illustrate distribution tendencies of the cells "cell" calculated by the density calculation unit 114. The horizontal axes of the graphs G1 to G3 show a total area Sg [$\mu m^2$] of one group of the cell region masks, and the vertical axes show a sum value of a number N of the cells "cell" included in the cell region mask corresponding to the total area Sg. Specifically, the density calculation unit 114 calculates a correspondence between the total area Sg of the one block of the cell region mask, and the sum value of the number N of the cells "cell" included in the cell region mask corresponding to the total area S. The correspondence calculated in this way is preferably displayed on a display unit, which is not illustrated. For example, in the graph G1, both the total area S of the cell region mask and the number N of cells "cell" are small values, and thus the cell density and the degree of cell adhesion can be evaluated as being small. Further, in the graph G2, the total area S of the cell region mask is a small value and the number N of cells "cell" is a large value, and thus the cell density can be evaluated as being large and the degree of cell adhesion can be evaluated as being small. Further, in the graph G3, both the total area S of the cell region mask and the number N of cells "cell" are large values, and thus the cell density and the degree of cell adhesion can be evaluated as being large.

In addition, the density calculation unit 114 calculates the degree of cell adhesion that represents a degree of adhesion between the cell "cell" and the cell "cell." For example, the density calculation unit 114 calculates the degree of cell adhesion by dividing the total area Sg of the largest block of the cell region mask by the total area S of the cell region mask of the whole region. In this way, as illustrated in FIG. 5, in the case of the region B and the region C that have the same number N of cells "cell" (the cell density), by calculating the degree of cell adhesion, the state of the cells present in the freely-selected regions can be quantitatively determined. As a result of this, from among the plurality of cells (hereinafter referred to as a cells group) cultivated in the culture vessel, the analysis device 100 can select the cells that are wished to be analyzed. Further, calculating the cell density and the degree of cell adhesion can be helpful in elucidating diseases, such as cancer metastasis, leukocyte adhesion deficiency and the like.

Note that here, the description is made in which the density calculation unit 114 performs the processing with respect to the images captured by the microscope 200, but the density calculation unit 114 may perform the processing with respect to images stored in advance in the storage unit 130, or with respect to images stored in advance in the external storage device 300.

Figure 6:
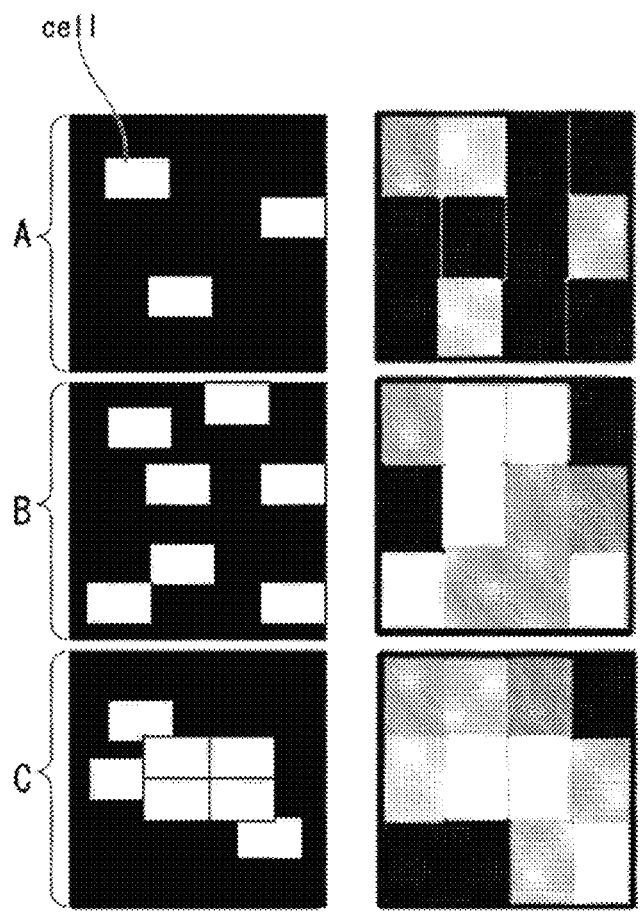
FIG. 6 is a diagram illustrating an example of a cell region mask created on the basis of low resolution images.

Further, the density calculation unit 114 may create the cell region mask on the basis of the images captured at the low resolution. FIG. 6 is a diagram illustrating an example of the cell region mask created on the basis of the low resolution images.

As illustrated in FIG. 6, in the captured low resolution images, the density calculation unit 114 detects an image (a square image configured by 4×8 pixels, for example) that is configured by a predetermined number of pixels that have a luminance value equal to or greater than the predetermined luminance value (a luminance value indicating the color black, for example). Specifically, in FIG. 6, the density calculation unit 114 creates the cell region mask in which the regions shown in black are "0," and the regions shown in other colors are "1." In this way, the density calculation unit 114 can calculate the cell density and the degree of cell adhesion.

Figure 7:
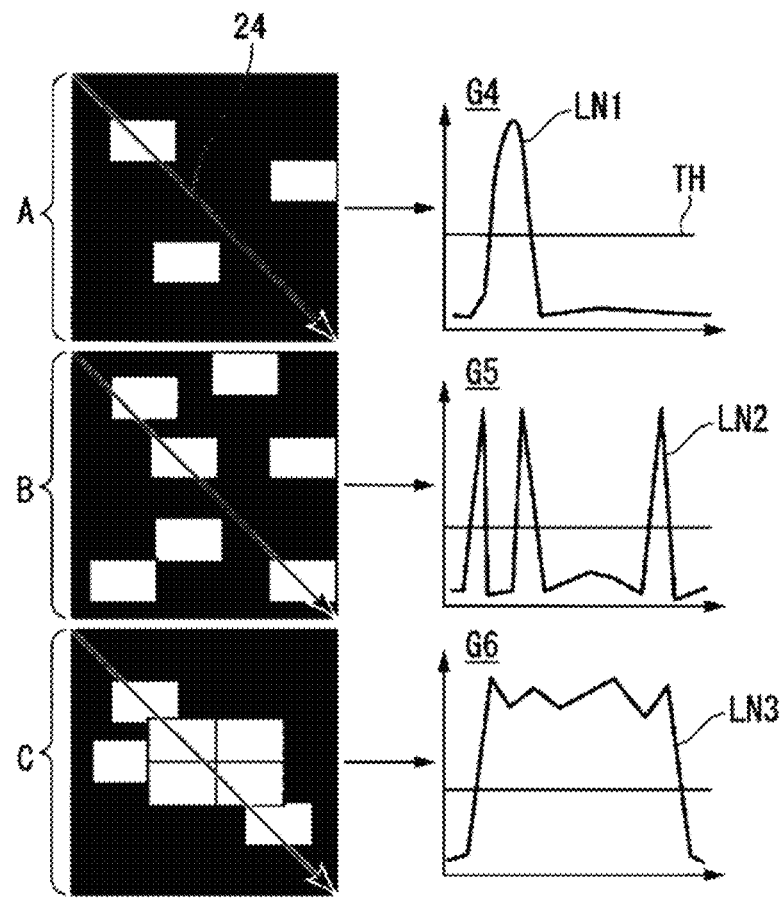
FIG. 7 is a diagram illustrating processing to calculate the number of luminance value peaks and an average luminance value on the basis of luminance values within a scanned range.

Further, the density calculation unit 114 may linearly scan the luminance values of the freely-selected regions, and may calculate the number of luminance value peaks and an average luminance value on the basis of the luminance values within the scanned range. FIG. 7 is a diagram illustrating processing to calculate the number of luminance value peaks and the average luminance value on the basis of the luminance values within the scanned range. As illustrated in FIG. 7, the density calculation unit 114 scans the luminance values along a direction indicated by arrows 24, in the freely-selected regions. Note that the direction in which the density calculation unit 114 scans the luminance values is not limited to the one direction and the density calculation unit 114 may perform a further scan in a direction orthogonal to the arrows 24, or the like.

For example, the density calculation unit 114 calculates, as the number of amplitude peaks, the number of times that the luminance values acquired as a result of the scanning exceed a predetermined luminance value TH. The density calculation unit 114 can express the luminance values obtained by the scanning by curved lines (LN1 to LN3) as illustrated in graphs G4 to G6. The horizontal axes of the graphs G4 to G6 show a range (where the unit is [$\mu m$]) of the straight line that is scanned, and the vertical axes show luminance values of pixels. As illustrated in the graph G4, when scanning is performed over a single fluorescing cell, the curved line LN1 indicating the luminance values obtained by the scanning is a curved line in which there is one amplitude peak. Further, as illustrated in the graph G5, when the scanning is performed over three of the fluorescing cells, for example, the curved line LN2 indicating the luminance values obtained by the scanning is a curved line in which there are three amplitude peaks. Further, as illustrated in the graph G6, when the scanning is performed over a plurality of the adjacent or overlapping fluorescing cells, for example, the curved line LN3 indicating the luminance values obtained by the scanning is a curved line in which there is one amplitude peak. Specifically, except for the case in which the fluorescing cells are adjacent to or overlapping with each other, there is a tendency for the number of the fluorescing cells present within the range of the scanning to be the same as the number of luminance value peaks shown in the graphs.

The density calculation unit 114 calculates the average luminance value from the luminance values obtained within the range of the scanning. The average luminance value is calculated by dividing the luminance values obtained by the scanning by the number of pixels present within the range of the scanning. From the graph G4, for example, the density calculation unit 114 can calculate an average luminance value of 10 (where an arbitrary unit is [arb.unit]), can calculate an average luminance value of 45 from the graph G5, and can calculate an average luminance value of 80 from the graph G4. As a result of this, under overall conditions including the case in which the fluorescing cells are adjacent to or overlapping with each other, the density calculation unit 114 can calculate the degree of cell adhesion easily, without creating the cell region mask, by calculating the number of amplitude peaks and the average luminance value.

Above, on the basis of the cell density and the degree of cell adhesion calculated by the processing of the density calculation unit 114, the regions that should be subject to actual observation can be derived.

On the basis of the cell density and the degree of cell adhesion calculated by the density calculation unit 114, the region of interest detection unit 116 detects regions of interest R (Region of Interest; ROI). The region of interest R is a region, from the region F representing the whole image of the culture vessel, that is detected as a target region on which the actual observation should be performed. The region of interest R corresponds to a "target location."

Figure 8:
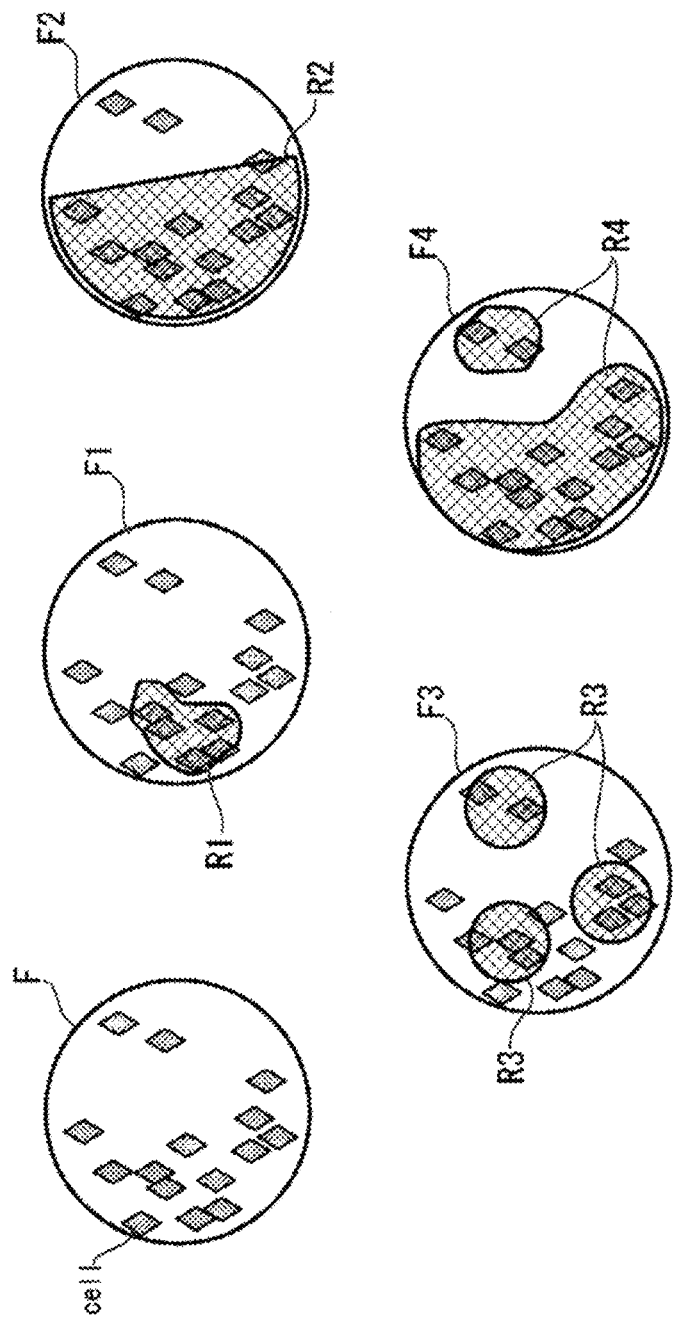
FIG. 8 is a schematic diagram illustrating an example of detection results of regions of interest R.

FIG. 8 is a schematic diagram illustrating an example of detection results of the regions of interest R. In a region F1, for example, the region of interest detection unit 116 detects, as a region of interest R1, a region in which the cell density and the degree of cell adhesion have exceeded threshold values (approximately 80% of each of those values, for example), set with respect to each of those values. Note that these threshold values are determined in advance by simulation, experimentation and the like.

In this way, the region that should be observed at the time of actual observation can be appropriately extracted. Further, since a region in which the cells are not present can be excluded from the region F representing the whole image of the culture vessel, the time for analysis processing can be shortened.

In addition, the region of interest detection unit 116 may detect, as the region of interest R, a region formed by a user. The region of interest R is formed, for example, by the user performing an input that specifies a prescribed region, using the input device (the mouse, the keyboard, the touch panel, or the like), which is not illustrated and is connected via the communication interface. In this case, the region of interest detection unit 116 detects, as the region of interest R, a region encompassed by a line having a predetermined line width input by the user. In this way, the region freely-selected by the user can be detected as the region of interest R.

Actual Observation

On the basis of the pre-observation results, the observation device 1 determines various parameters at a time of image capture, and captures a high resolution image of the region of interest R using those parameters. Specifically, the microscope control unit 112 controls the microscope 200 so as to capture an image of the region of interest R at a high magnification. At this time, when the conditions of the object targeted by the actual observation match or are similar to past data stored in the storage unit 130 or the like, the observation device 1 may apply, as the image capture parameters for the actual observation, parameters applied at the time of image capture when the stored data have been obtained. Further, the observation device 1 may automatically measure the SN ratio (the Signal-Noise ratio) of the image and improve the precision of the observation. Hereinafter, processing by the analysis device 100 at the time of actual observation will be described.

Separation 1 of Cells on Image

From the image captured by the microscope 200, the cell region separation unit 118 detects the cell regions and separates the cells. For example, the cell region separation unit 118 detects the cell region per single cell, from the transmission DIC image, the phase contrast image, the dark field image, the bright field image, and the colored image obtained from the same cell group. The colored image is, for example, an image indicating that at least one of the cell as a whole, the cytoplasm, the cell membrane, the nucleus, an organelle group inside the cell, and biological material have been colored using a fluorescent dye reagent, antibodies or the like.

Figure 9:
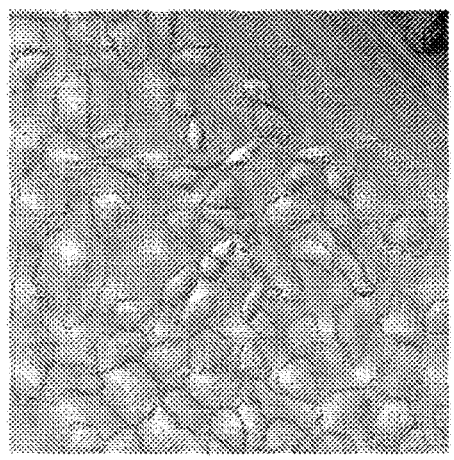
FIG. 9 is a diagram illustrating an example of a transmission DIC image 30 and a colored image 32.
Figure 9:
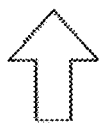
Figure 9:
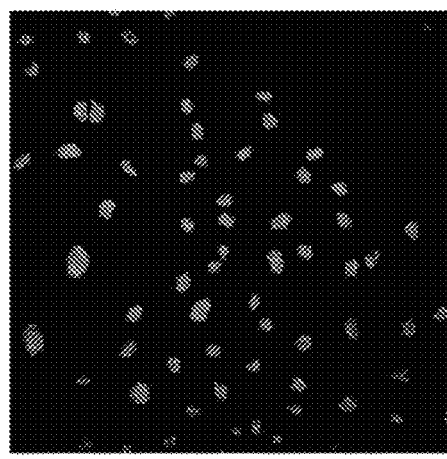
Figure 9:
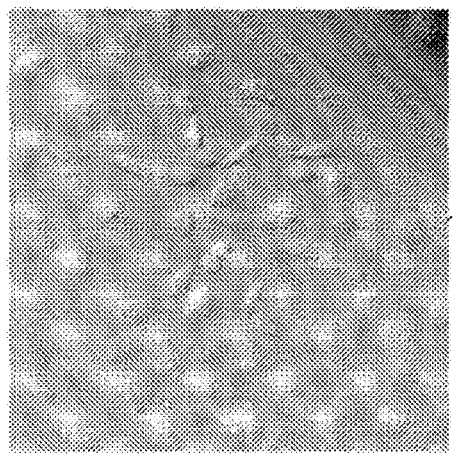

Here, an example of processing of the cell region separation unit 118 will be described with reference to FIG. 9. FIG. 9 is a diagram illustrating an example of a transmission DIC image 30 and a colored image 32.

For example, the cell region separation unit 118 overlays the transmission DIC image 30 and the colored image 32 captured by the microscope 200. From the overlaid transmission DIC image 30 and colored image 32, the cell region separation unit 118 detects the cell membranes and the colored nuclei. When the degree of adhesion between the cells is extremely high and a boundary between the cells is indistinct, the cell region separation unit 118 separates the cells, on the image, such that one of the detected colored nuclei is present inside each of the cell membranes. More specifically, the cell region separation unit 118 separates the cells such that distances between the nuclei are equal. The cell region separation unit 118 detects the cell regions by calculating an area inside the separated cells. The cell region separation unit 118 calculates an average value of the areas of all of the detected cell regions, and stores the average value in the storage unit 130.

Alternatively, the cell region separation unit 118 may detect the cell regions on the basis of a single one of the transmission DIC image, the phase contrast image, the bright field image, or the dark field image, as the image captured by the microscope 200. For example, the cell region separation unit 118 sharpens the transmission DIC image 30 so as to be able to detect the cell membranes and the nuclei. The sharpening is processing that converts the image to a clear image, using a differential filter or the like. The cell region separation unit 118 detects the cell membranes and the nuclei from the sharpened image. In this way, the cell region separation unit 118 can separate the cells and detect the cell regions by calculating an area inside the separated cells. Further, since the cells have been colored using the fluorescent dye reagent, an enzyme, or the like, a harmful influence on the cells can be minimized.

In addition, when part of the detected cell membrane is broken, the cell region separation unit 118 may perform appropriate processing, join up the broken cell membrane, and separate the cells. Further, the cell region separation unit 118 may separate the cells by performing machine learning, on the basis of information stored in the storage unit 130, the external storage device 300, or the like. In this way, the separation of the cells can be more precisely performed.

Separation II of Cells on Image

Figure 10:
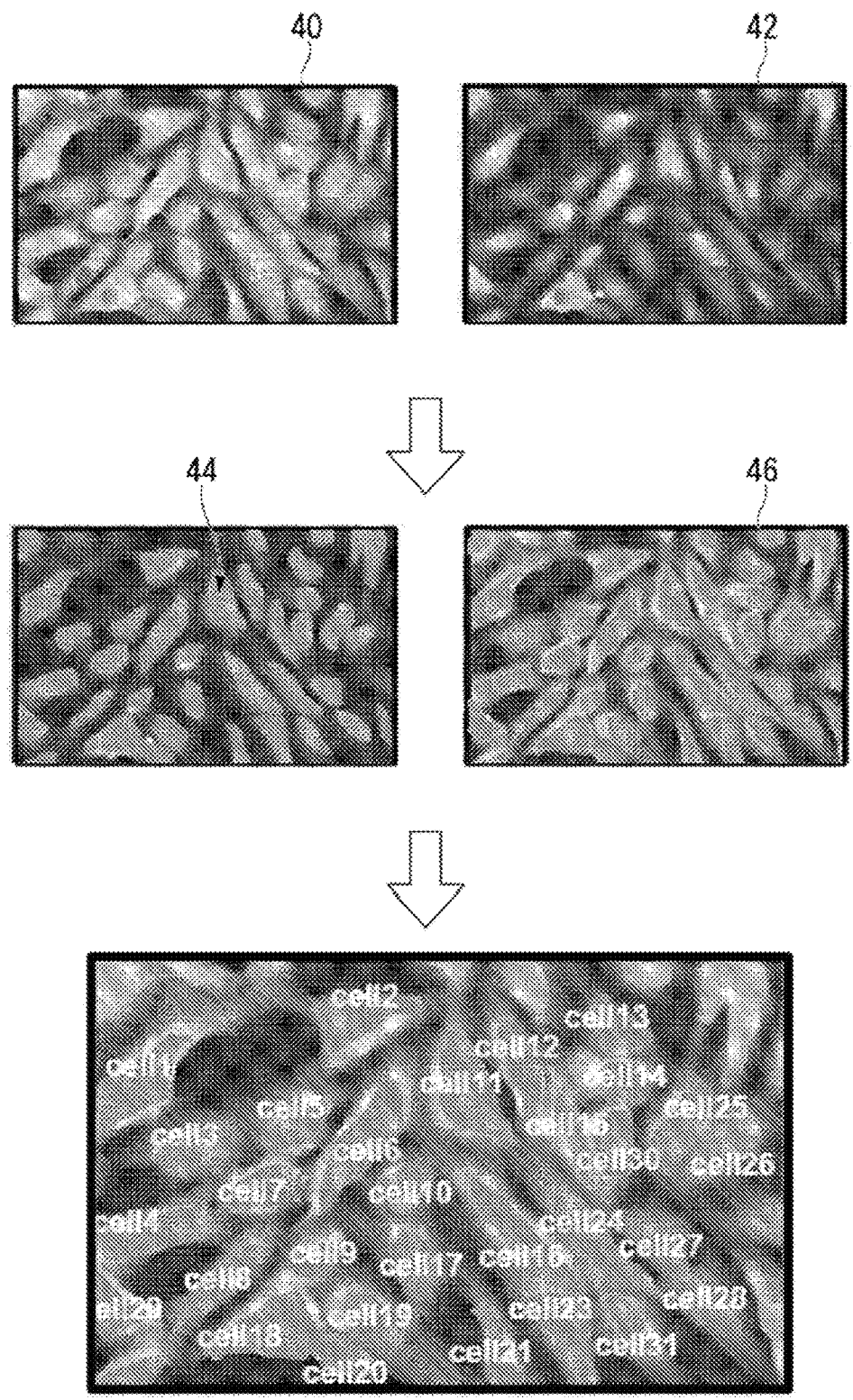
FIG. 10 is a diagram illustrating an example of cell region detection processing performed with respect to a colored image.

Alternatively, the cell region separation unit 118 may detect the cell regions on the basis of the colored image. FIG. 10 is a diagram illustrating an example of cell region detection processing performed with respect to a colored image.

The cell region separation unit 118 creates a cell region mask 44, on the basis of a colored image 40 or a colored image 42 each captured at a predetermined focal position. The predetermined focal position is, for example, the best focal position, or a position that is displaced from the best focal position by a predetermined correction quantity in a positive direction (or a negative direction) of a Z axis. The predetermined correction quantity is calculated in advance, in accordance with the state of the cell that is one of the analysis targets (elements), and is stored in advance in the storage unit 130, the external storage device 300, or the like.

As a result of the processing to separate these cells, the cell region detection can be performed with respect to the cell group cultivated in the culture vessel. Further, the cell region detection can be performed even when the degree of adhesion and the density of the cell group are large.

Processing to Correct Luminance Value

Figure 11:
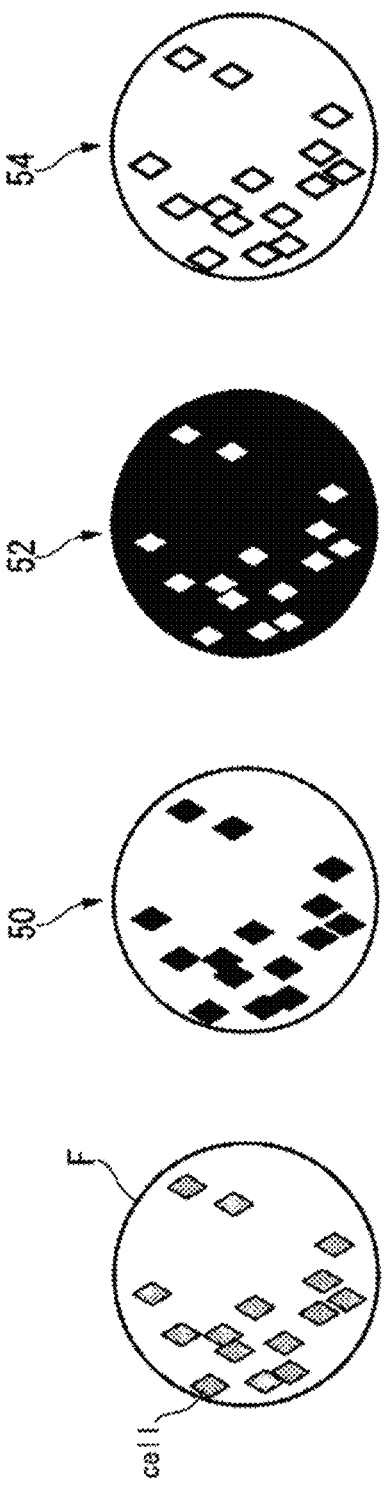
FIG. 11 is a diagram illustrating an example of processing to correct the luminance values.

Before extracting the characteristic quantities, the analysis device 100 may perform the following processing in advance with respect to each of the cells separated on the image. FIG. 11 is a diagram illustrating an example of processing to correct the luminance value.

The luminance correction unit 120 corrects the luminance of the background region, in the region F representing the whole image of the culture vessel. For example, the luminance correction unit 120 creates a cell region mask 50, from the cell regions indicating the regions of the cells "cell" separated by the cell region separation unit 118, in the region F representing the whole image of the culture vessel. Further, the luminance correction unit 120 creates a background region mask 52 from the background region representing the regions in which the cell regions have been subtracted from the region F. The luminance correction unit 120 calculates the average luminance value of the whole of the created background region mask 52. The luminance correction unit 120 corrects the luminance value of the background region, by subtracting the calculated average luminance value from the luminance values of each of the pixels configuring the created cell region mask 50.

Alternatively, the luminance correction unit 120 may correct the luminance value of the background region by processing described below. For each of the cells "cell" separated by the cell region separation unit 118, the luminance correction unit 120 calculates the average luminance value of a background region mask 54 in the vicinity of each of those cells "cell." "In the vicinity" refers to being within 5 pixels, for example, from an outermost pixel among the pixels representing the cells "cell." Specifically, the luminance correction unit 120 calculates the average luminance value of a part of the background region mask 54 that surrounds a contour of the cell "cell." The luminance correction unit 120 corrects the luminance value of the background region, by subtracting the calculated average luminance value from the luminance values of each of the pixels configuring the created cell region mask 50.

In this way, conventional processing, in which the background region is corrected by comparing a captured image of the culture vessel in which the cells are not present with a captured image of the culture vessel in which the cells are present, becomes unnecessary. As a result, the analysis processing can be even more easily performed. Further, at the time of image capture of the culture vessel, when irregularities occur in the luminance value due to peripheral darkening, unevenness in the sensitivity of the microscope or the like, by correcting the luminance value of the background region, the image as a whole can be caused to have an even brightness on average. As a result, the characteristic quantities can be extracted more accurately.

Separation III of Cells on Image

Figure 12:
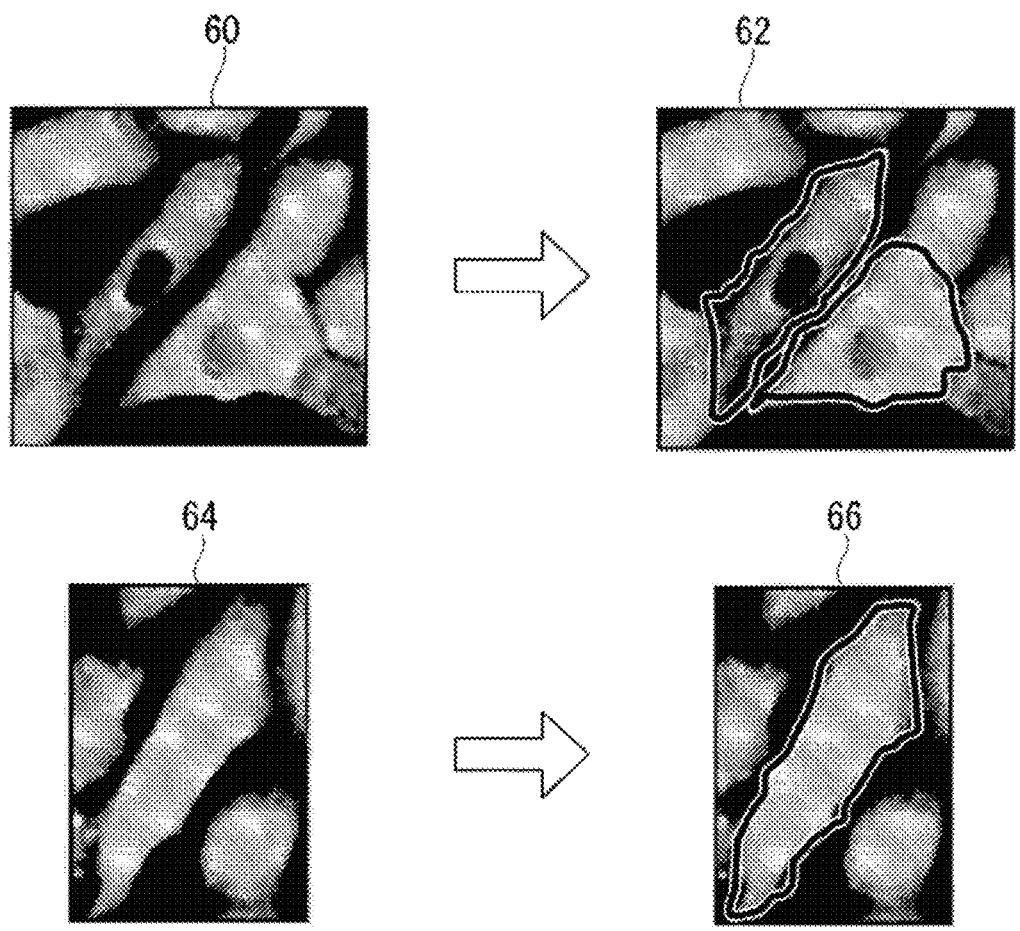
FIG. 12 is a diagram illustrating examples of images of cells that have been colored.

The cell region separation unit 118 detects a predetermined color pattern from the image of the colored analysis target, and selects, with respect to the image of the analysis target, an optimum cell region detection method that is associated in advance with the predetermined color pattern. For example, the cell region separation unit 118 detects the predetermined color pattern on the basis of a variance value of the luminance values of the image. FIG. 12 is a diagram illustrating an example of images of colored cells.

When the cell region separation unit 118 detects an image 60 of a cell nucleus detection pattern as the predetermined color pattern, the cell region separation unit 118 acquires a predetermined method that is associated with a cell nucleus dark color pattern, from among the cell region detection methods stored in advance in the storage unit 130. The cell nucleus detection pattern is a color pattern when the nucleus can be detected, as a result of a difference occurring between the luminance values in the region of the image representing the nucleus of the cell and in the region of the image of the nucleus periphery. On the basis of the predetermined method acquired from the storage unit 130, the cell region separation unit 118 separates the cell membranes on the image, and calculates the individual cell regions (an image 62, for example).

When the cell region separation unit 118 detects an image 64 of a cell nucleus non-detection pattern as the predetermined color pattern, for example, the cell region separation unit 118 acquires a predetermined method that is associated with a cell nucleus non-detection pattern, from among the cell region detection methods stored in advance in the storage unit 130. The cell nucleus non-detection pattern is a color pattern when the nucleus cannot be detected, as a result of the luminance values between the region of the image representing the nucleus of the cell and the region of the image of the nucleus periphery being substantially the same. On the basis of the predetermined method acquired from the storage unit 130, the cell region separation unit 118 separates the cells on the image, and calculates the individual cell regions (an image 66, for example).

In this way, even if the user does not have any knowledge relating to cell analysis, the user can separate the cells on the image, and calculate the individual cell regions. Further, the time required for the processing to separate the cells can be shortened.

Note that, here, the optimum cell region detection methods associated in advance with the predetermined color patterns are stored in the storage unit 130, but the configuration is not limited to this example. For example, the methods may be stored in the external storage device 300 or another storage device.

In addition, here, the methods associated in advance with the predetermined color patterns are the optimum cell region detection methods, but the methods may be methods for detecting various characteristic quantities or methods for detecting the analysis targets (the elements) themselves.

Hereinafter, processing performed at the time of analysis will be described. It is assumed that the cells that are one of the analysis targets (the elements) are separated in advance on the image, and the cell regions are already calculated. Here, an example is given below for quantitatively analyzing various phenomena.

Analysis of Protein Localization

With respect to the cells separated by the cell region separation unit 118 in a section inside the region of interest detected by the region of interest detection unit 116, the characteristic quantity extraction unit 122 extracts the characteristic quantities of substances passing between the nucleus of the cell and the cytoplasm. Note that these substances are fluorescently dyed in advance using antibodies, fluorescent proteins, or the like. For example, the characteristic quantity extraction unit 122 extracts the characteristic quantities of a protein, which is the substance passing between the nucleus of the cell and the cytoplasm. For example, when the protein localized in the nucleus has moved to the cytoplasm that covers the exterior of the nucleus, the characteristic quantity extraction unit 122 extracts, from the images before and after the movement of the protein, the following values as the characteristic quantities. Further, even when the protein localized in the cytoplasm has moved into the nucleus, the characteristic quantity extraction unit 122 extracts the characteristic quantities from the images before and after the movement of the protein. Note that the characteristic quantities described below are an example and other characteristic quantities may be extracted.

Sum of luminance values of nucleus/sum of luminance values of cytoplasm
    Sum of luminance values of nucleus/sum of luminance values of cell
    Average luminance value of nucleus/average luminance value of cytoplasm
    Average luminance value of nucleus/average luminance value of cell
    Dispersion of luminance values inside cell
    Dispersion of luminance values inside nucleus
    Average of luminance values inside nucleus
    Dispersion of luminance values inside cytoplasm
    Average of luminance values inside cell
    Average of luminance values inside cytoplasm
    Median luminance value of nucleus/median luminance value of cytoplasm
    Median luminance value of nucleus/median luminance value of cell
    Median value of luminance values inside cell
    Median value of luminance values inside nucleus
    Median value of luminance values of cytoplasm Furthermore, the characteristic quantity extraction unit 122 may extract the characteristic quantities of the substances passing between the nuclear membrane of the cell and the nucleus of the cell, or the characteristic quantities of the substances passing between the nuclear membrane of the cell and the cytoplasm. For example, the characteristic quantity extraction unit 122 extracts the characteristic quantities of the protein Nup98 or the like, as the substance passing between the above-described cell structures. For example, when the protein localized inside the nuclear membrane of the cell (the nucleus of the cell) has moved to the nucleus of the cell (the nuclear membrane of the cell), or when the protein localized in the nuclear membrane of the cell (the cytoplasm) has moved to the cytoplasm (the nuclear membrane of the cell), the characteristic quantity extraction unit 122 extracts the following values as the characteristic quantities from the images before and after the movement of the protein. Note that the characteristic quantities described below are an example and other characteristic quantities may be extracted.

Sum of luminance values of nuclear membrane/sum of luminance values of nucleus
    Average luminance value of nuclear membrane/average luminance value of nucleus
    Dispersion of luminance values inside nucleus
    Number of bright spots inside cytoplasm
    Average luminance value of bright spots inside cell
    Sum of luminance values of bright spots inside cell (total value for each cell)
    Area of each bright spot
    Average area of bright spots for each cell
    Median luminance value of nuclear membrane/median luminance value of nucleus
    Sum of luminance values of nuclear membrane/sum of luminance values of cytoplasm
    Average luminance value of nuclear membrane/average luminance value of cytoplasm
    Median luminance value of nuclear membrane/median luminance value of cytoplasm
    Sum of luminance values of nuclear membrane/sum of luminance values of cell
    Average luminance value of nuclear membrane/average luminance value of cell
    Median luminance value of nuclear membrane/median luminance value of cell
    Sum of luminance values of nuclear membrane
    Average luminance value of nuclear membrane
    Luminance dispersion of nuclear membrane
    Median value of nuclear membrane
    Dispersion of luminance values inside cytoplasm
    Average of luminance values inside cell
    Average of luminance values inside cytoplasm
    Median luminance value of nucleus/median luminance value of cytoplasm
    Median luminance value of nucleus/median luminance value of cell
    Median value of luminance values inside cell
    Median value of luminance values inside nucleus
    Median value of luminance values of cytoplasm Analysis I of Formation of Protein Aggregate When a substance distributed uniformly in the predetermined region of the cell is formed so as to aggregate (become a spot), the characteristic quantity extraction unit 122 extracts the characteristic quantities of the substance from images before and after the aggregation. For example, the characteristic quantity extraction unit 122 extracts the characteristic quantities from a protein such as GSK3β or p-GSK3β, as the substance distributed uniformly in the predetermined region of the cell. For example, the characteristic quantity extraction unit 122 extracts the following values as the characteristic quantities, from the images before and after the aggregation of the protein. Note that the characteristic quantities described below are an example and other characteristic quantities may be extracted.

Sum of luminance values of nucleus/sum of luminance values of cell
    Sum of luminance values of nucleus/sum of luminance values of cytoplasm
    Average luminance value of nucleus/average luminance value of cell
    Average luminance value of nucleus/average luminance value of cytoplasm
    Dispersion of luminance values inside cell
    Number of spots
    Number of spots inside nucleus/number of spots outside nucleus Analysis II of Formation of Protein Aggregate When the substance uniformly distributed in the predetermined region of the cell partially aggregates and forms a specific aggregate (a domain), the characteristic quantity extraction unit 122 extracts the characteristic quantities of the substance forming the specific aggregate (domain). For example, the characteristic quantity extraction unit 122 extracts the characteristic quantities of the protein that is the substance forming the specific aggregate (domain). The protein is, for example, Actin, SNX-9, p-Akt (S473), WASH1, EEA1 and the like. For example, the characteristic quantity extraction unit 122 extracts the following values as the characteristic quantities, from the image before and after the protein forms the specific aggregated (domain). Note that the characteristic quantities described below are an example and other characteristic quantities may be extracted.

Dispersion of Luminance Values of Cytoplasm
    Area of domain
    Number of domains inside cell (total value and average value for each cell)

Sum of luminance values of domain/sum of luminance values of cytoplasm

Average luminance value of domain/average luminance value of cell

Analysis of Protein Colocalization

When the substance uniformly distributed in the predetermined region of the cell partially aggregates and forms the specific aggregate (domain), the characteristic quantity extraction unit 122 extracts the characteristic quantities of another substance that aggregates in the same location as the specific aggregate (domain). Further, when the specific aggregate is not formed, the characteristic quantity extraction unit 122 analyzes whether or not a plurality of substances are present in the same location by extracting the characteristic quantities of those substances. For example, the characteristic quantity extraction unit 122 extracts the characteristic quantities of the protein that is the substance aggregating in the same location as the specific aggregate (domain).

For example, when the actin that is one type of protein forms the domain (hereinafter referred to as an "actin domain"), the characteristic quantity extraction unit 122 extracts the characteristic quantities from the luminance values of the protein distributed in a constant range of the periphery of the domain. The characteristic quantity extraction unit 122 extracts the following values as the characteristic quantities of the luminance values of the protein. Note that the characteristic quantities described below are an example and other characteristic quantities may be extracted.

Dispersion of luminance values of protein in constant range of actin domain periphery Sum of luminance values of protein on actin domain/sum of luminance values of protein of whole cell Average luminance value of protein on actin domain/ average luminance value of protein of whole cell Sum of luminance values of protein in constant range of actin domain periphery/sum of luminance values of protein of whole cell Average luminance value of protein on actin domain/ average luminance value of protein in constant range of domain periphery Sum of luminance values of protein on actin domain/sum of luminance values of protein in constant range of domain periphery Further, for example, when the actin and another protein form the domains, the characteristic quantity extraction unit 122 extracts the following values as the characteristic quantities, on the basis of the formed domains. Note that the characteristic quantities described below are an example and other characteristic quantities may be extracted.

Area of region over which actin domain and protein domain overlap/area of total regions of actin domain and protein domain Dispersion of luminance values of protein in constant range of actin domain periphery Analysis of Directionality of Microfilaments In some cases, when the cell moves and becomes active, the cell changes the shape thereof. At this time, the actin, which is the one type of protein present inside the cell, or microfilaments of microtubules and the like, indicate a specific directionality in accordance with the change in the cell. These microfibers can be fluorescently dyed using antibodies, fluorescent proteins, and the like.

Figure 13:
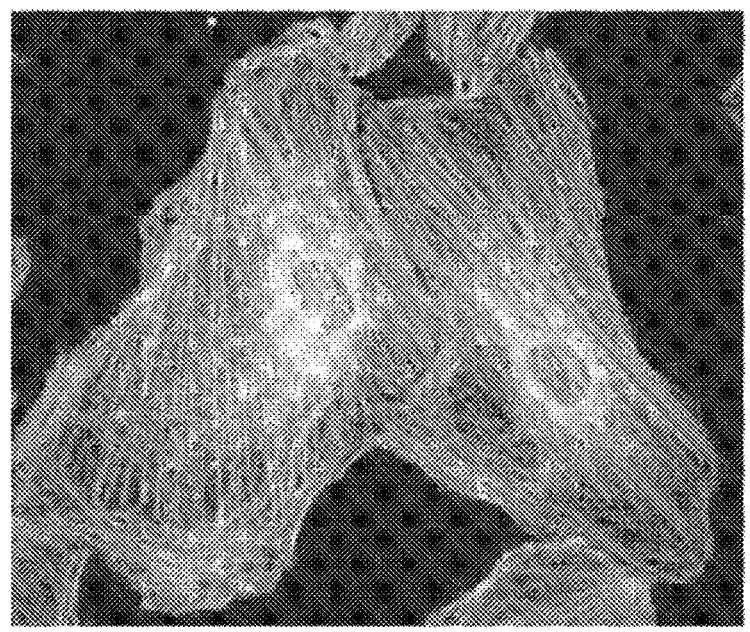
FIG. 13 is a diagram illustrating an example of microfilaments inside a cell.
Figure 13:
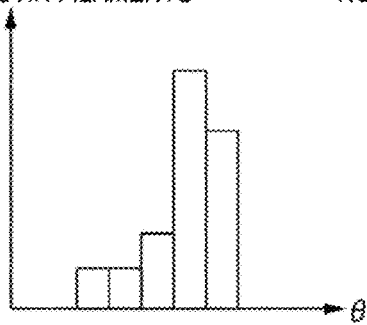
Figure 13:
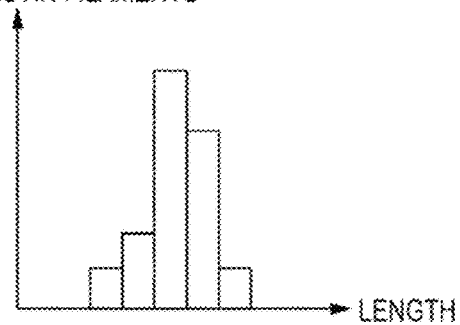
Figure 13:
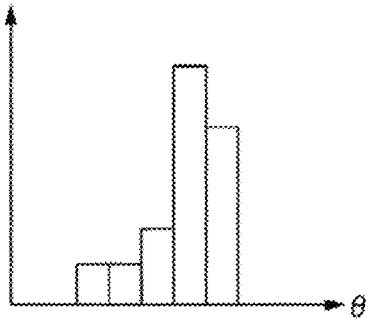
Figure 13:
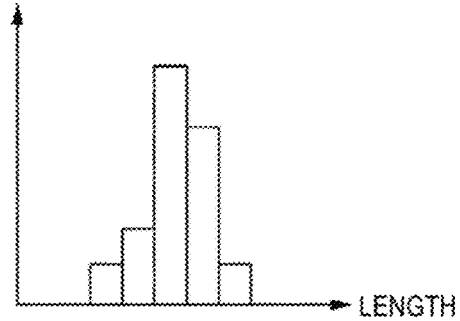

The characteristic quantity extraction unit 122 extracts the characteristic quantities of the microfilaments present inside the cell, from the before and after images indicating the directionality of the microfilaments. FIG. 13 is a diagram illustrating an example of the microfilaments inside the cell. The characteristic quantity extraction unit 122 extracts, as the characteristic quantities, vectors and angles θ, from the microfilaments having directionality inside the cell.

The characteristic quantity extraction unit 122 calculates the number of the microfilaments having directionality and the angles θ of the microfilaments having directionality. A graph G7 is a histogram configured from the number of the microfilaments having directionality and the angles θ of the microfilaments having directionality.

Further, the characteristic quantity extraction unit 122 calculates the number of cells having the microfilaments inside, and statistical values of the angles θ of the microfilaments for each cell. A graph G8 is a histogram configured from the number of cells having the microfilaments inside, and statistical values of the angles θ of the microfilaments for each cell.

In addition, the characteristic quantity extraction unit 122 calculates the number of the microfilaments having directionality, and lengths of the microfilaments having directionality. A graph G9 is a histogram configured from the number of the microfilaments having directionality, and the lengths of the microfilaments having directionality.

Further, the characteristic quantity extraction unit 122 calculates the number of cells having the microfilaments inside, and statistical values of the lengths of the microfilaments for each cell. A graph G9 is a histogram configured from the number of the cells having the microfilaments inside, and the statistical values of the lengths of the microfilaments for each cell. Note that all of the above-described histograms are created for each of the cells under the same conditions.

In this way, cell migration can be quantitatively analyzed. As a result, when information with respect to the directionality of the cells is obtained in advance, the cells can be identified.

Analysis of Aggregation of Protein Complex

Protein complexes, such as chromatin, that are uniformly distributed inside the nucleus of the cell form small lumps and aggregate when the cell dies. These proteins can be fluorescently dyed using antibodies, fluorescent proteins, or fluorescent dyes (DAPI, Hoechst and the like, for example).

Figure 14:
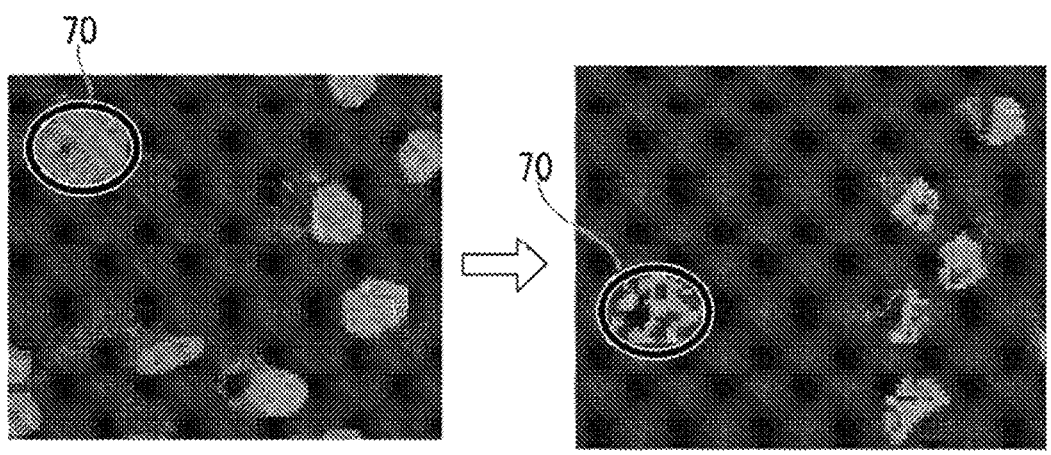
FIG. 14 is a diagram illustrating an example of a protein complex.

The characteristic quantity extraction unit 122 extracts, as the characteristic quantities, a degree of aggregation of the protein complex, from the images before and after the aggregation of the protein complex. FIG. 14 is a diagram illustrating an example of a protein complex. For example, the characteristic quantity extraction unit 122 extracts a dispersion of the luminance values of the whole region of a nucleus 70 detected by the cell region separation unit 118, as the characteristic quantities indicating the degree of aggregation of the protein complex. In this way, the protein complex aggregate can be quantitatively analyzed. Accordingly, this can be helpful when elucidating phenomena at the time of cell death.

Figure 15:
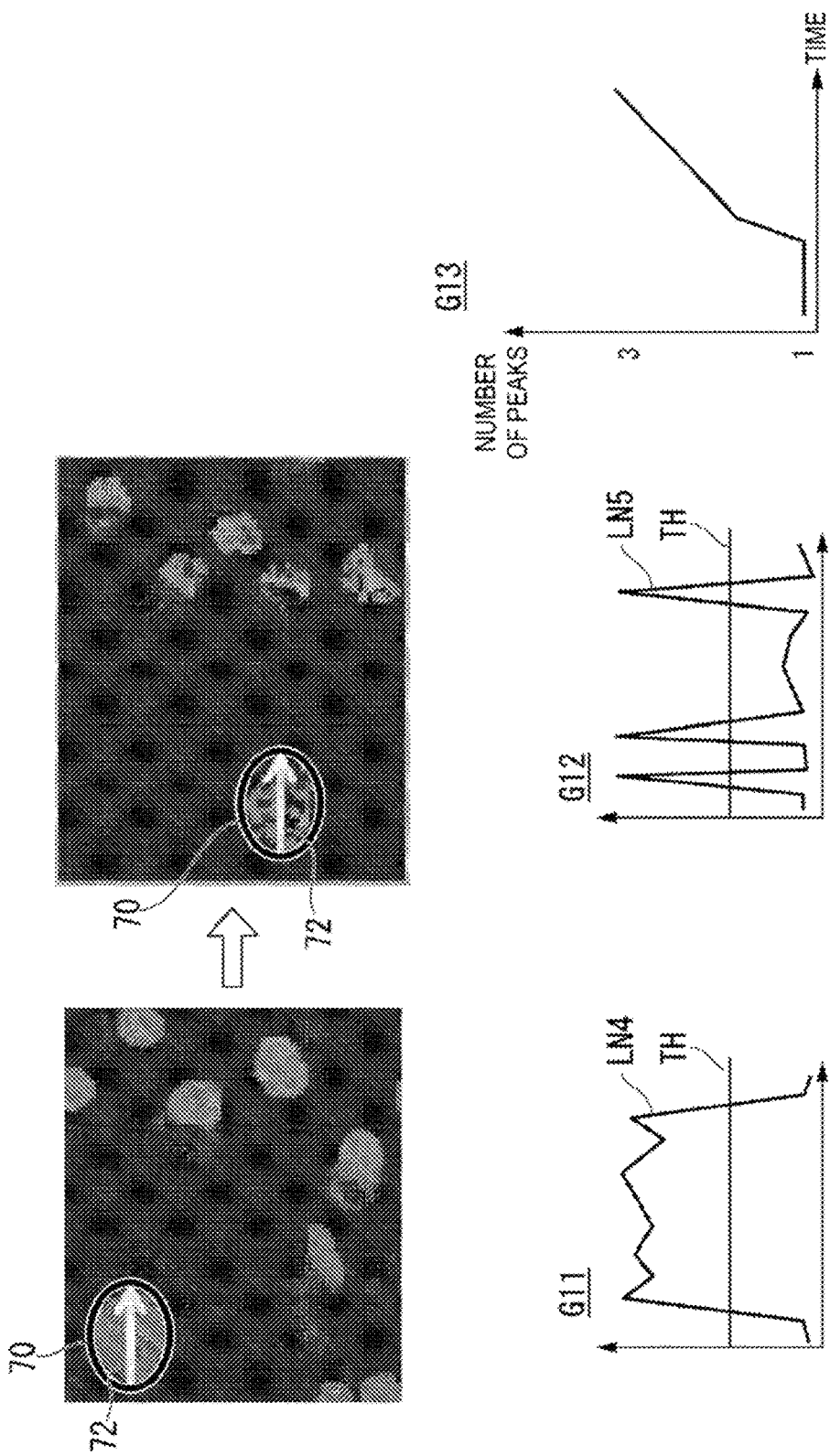
FIG. 15 is a diagram illustrating an example of processing to linearly scan luminance values, with respect to images of the protein complex before and after aggregation.

Further, the characteristic quantity extraction unit 122 may linearly scan the luminance values of the nucleus 70 detected by the cell region separation unit 118, and may calculate the number of luminance value peaks and the average luminance value on the basis of the luminance values inside the scanned range. FIG. 15 is a diagram illustrating an example of processing to linearly scan the luminance values, with respect to images of the protein complex before and after the aggregation. As illustrated in FIG. 15, the characteristic quantity extraction unit 122 scans the luminance values of the nucleus 70 along a direction indicated by arrows 72. Note that the direction along which the characteristic quantity extraction unit 122 scans the luminance values of the nucleus 70 is not limited to the one direction and may perform a further scan in a direction orthogonal to the arrows 72, or the like.

The characteristic quantity extraction unit 122 calculates, as the number of amplitude peaks, a number of times that the luminance values obtained by scanning exceed the predetermined luminance value TH. The luminance values obtained by the scanning of the characteristic quantity extraction unit 122 can be expressed using curved lines (LN4 and LN5) as illustrated in graphs G11 and G12. The horizontal axes of the graphs G11 and G12 show a range (where the unit is [µm]) of a straight line that is scanned, and the vertical axes show the luminance values of pixels. As illustrated in the graph G11, when the protein complex is uniformly distributed inside the nucleus 70, the curved line LN4 indicating the luminance values obtained by the scanning is a curved line, for example, in which there is one amplitude peak. As illustrated in the graph G12, when the protein complex is aggregated inside the nucleus 70, the curved line LN5 indicating the luminance values obtained by the scanning is a curved line, for example, in which there are three amplitude peaks. In this way, it can be determined that the number of amplitude peaks increases as the aggregation of the protein complex advances. Further, when a process of aggregation of the protein complex is analyzed by images in a time-series, a graph G13, in which time and the number of amplitude peaks are expressed, can be illustrated. In this way, the protein complex aggregate can be quantitatively analyzed.

In addition, the characteristic quantity extraction unit 122 may extract the characteristic quantities relating to a spatial sequence, from the images representing the analysis targets (the cells, for example). The characteristic quantities relating to the spatial sequence are, for example, coordinate information on the image, or a distance between a plurality of the analysis targets, and the like.

In this way, at the time of processing to visualize the analysis targets, perform imaging or image analysis and the like, the characteristic quantities relating to the spatial sequence can be used as one index.

Analysis I of Mechanisms

On the basis of data expressing various characteristic quantities (hereinafter referred to as "characteristic data"), which are extracted by the characteristic quantity extraction unit 122 in accordance with a time series or with changes in the peripheral environment of the cell such as stimulation conditions and the like, or in accordance with changes in the state of the cell resulting from an elapsed period of time from a differentiation stage or from the stimulus, or resulting from gene expression, the mechanism analysis unit 124 calculates correlations between the characteristic data. In the present embodiment, for example, a plurality of the characteristic data are created with respect to a single one of the analysis targets (elements). For example, from an element a, characteristic data a1 to an are each created, and from an element b, characteristic data b1 to bn are each created. Note that a description of elements c onward is omitted here. Here, n is assumed to represent a positive integer.

For example, when the element is the cell, the characteristic data are created as data expressing the characteristic quantities of the morphology, speed, directionality (migration direction), and the like. Further, for example, when the element is the organelle, the characteristic data are created as data expressing the characteristic quantities of the morphology, distribution, and the like. Further, for example, when the element is the biological material, the characteristic data are created as data expressing the characteristic quantities of expression, localization, colocalization, aggregation, and the like. Further, for example, when the element is a structure inside the nucleus, the characteristic data are created as data expressing the characteristic quantities of the morphology, distribution, and the like. Further, for example, when the element is a specific gene or is associated with that gene product, the characteristic data are created as data expressing the characteristic quantities of the gene expression, localization, colocalization, and aggregation of the gene product, and the like.

Figure 16:
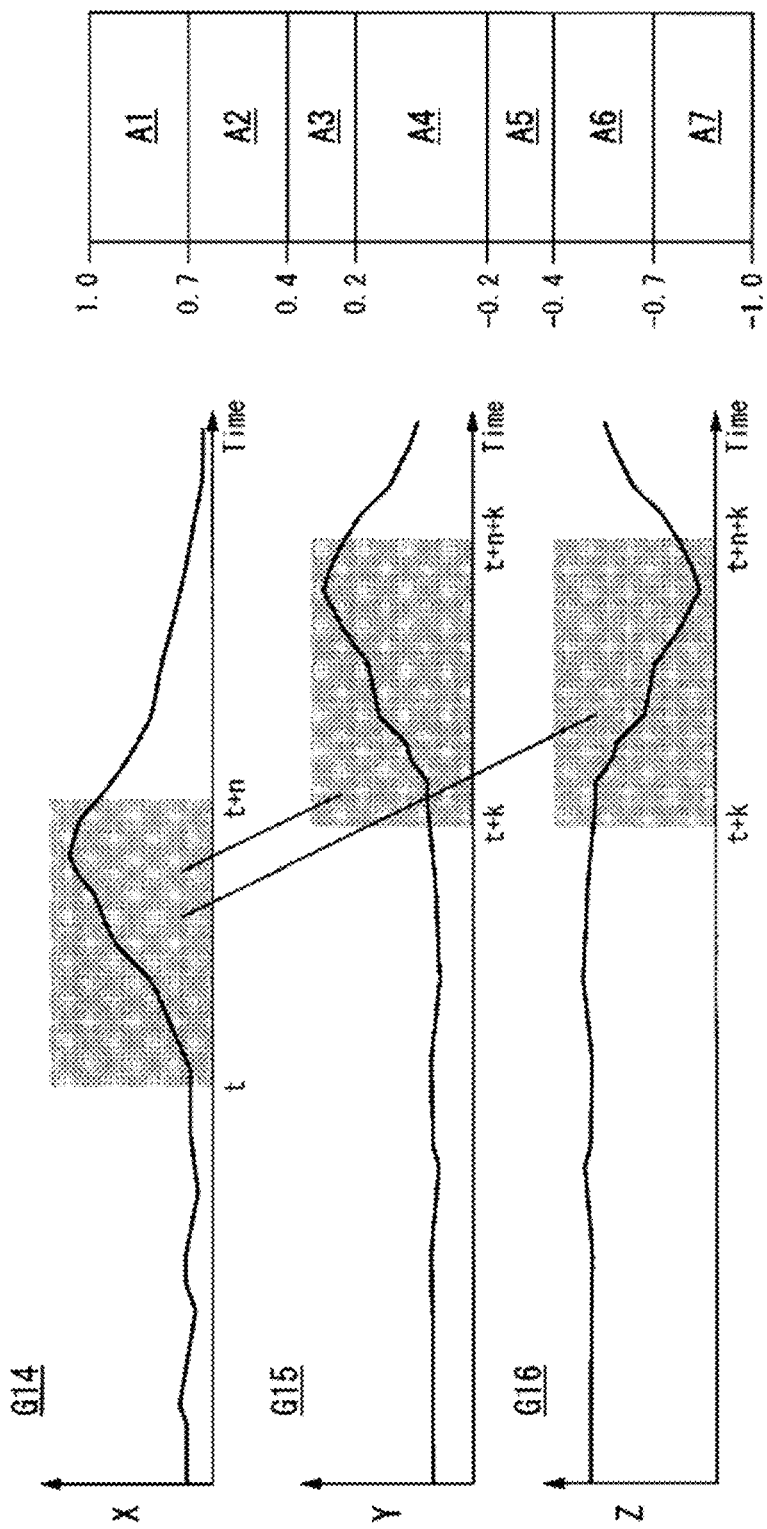
FIG. 16 is a diagram illustrating examples of characteristic quantities extracted in time series by a characteristic quantity extraction unit 122.

FIG. 16 is a diagram illustrating an example of the characteristic quantities extracted in time series by the characteristic quantity extraction unit 122. For example, the mechanism analysis unit 124 calculates correlations between characteristic data X that change over time as illustrated in a graph G14, characteristic data Y that change over time as illustrated in a graph G15, and characteristic data Z that change over time as illustrated in a graph G16, on the basis of Equations (1) and (2) shown below. The characteristic quantities are expressed, for example, as a length n, and a time difference k. Equation (1) is an equation for calculation that calculates a cross covariance $C_k$, and Equation (2) is an equation for calculation that calculates a cross correlation $R_k$.

Equation 1

$$C_k = \frac{1}{n}\sum_{t=1}^{n}(x_t - \bar{x})(y_{t+k} - \bar{y}) \quad (1)$$

Equation 2

$$R_k = \frac{C_k}{\sqrt{\frac{1}{n}\sum_{t=1}^{n}(x_t - \bar{x})^2}\sqrt{\frac{1}{n}\sum_{t=1}^{n}(y_{t+k} - \bar{y})^2}} \quad (2)$$

First, the correlation between the characteristic data X and Y will be described.

For example, the mechanism analysis unit 124 calculates the correlation between the characteristic data X and the characteristic data Y by comparing a section in which an amount of change of the characteristic data X is large (t to t+n), and a section in which an amount of change of the characteristic data Y is large (t+k to t+k+n). At this time, the correlation between the characteristic data X and the characteristic data Y is calculated, for example, as a correlation coefficient 0.9 (a positive correlation). For example, with respect to the characteristic data, the mechanism analysis unit 124 samples values of the characteristic data over a constant pitch width, and identifies a section in which a difference between temporally adjacent data is equal to or greater than a threshold quantity as the section in which the amount of change is large.

For example, the mechanism analysis unit 124 calculates the correlation by comparing the characteristic data X extracted when a protein (FoxO1) localized inside the nucleus has moved to the cytoplasm that covers the outside of the nucleus, with the characteristic data Y extracted when a protein (Nup98) localized in the nuclear membrane moves to the inside of the nucleus.

For example, the mechanism analysis unit 124 builds a hypothesis in which the changes in the characteristic data Y have been caused by the changes in the characteristic data X, as illustrated in FIG. 16. The phrase "builds a hypothesis" refers to writing information representing the correlation between provisional characteristic data into the storage unit 130, and making various selections in subsequent processing. In other words, the mechanism analysis unit 124 calculates the correlation between the provisional characteristic data while taking the characteristic data X as main data and the characteristic data Y as secondary data.

Next, the correlation between the characteristic data X and Z will be described.

For example, the mechanism analysis unit 124 calculates the correlation between the characteristic data X and the characteristic data Z by comparing the section in which the amount of change of the characteristic data X is large (t to t+n), and a section in which an amount of change of the characteristic data Z is large (t+k to t+k+n). In the example illustrated in FIG. 16, the correlation between the characteristic data X and the characteristic data Z is calculated, for example, as a correlation coefficient −0.9 (a negative correlation).

For example, the mechanism analysis unit 124 builds a hypothesis in which the changes in the characteristic data Z have been caused by the changes in the characteristic data X, as illustrated in FIG. 16. In other words, the mechanism analysis unit 124 calculates the correlation between the characteristic data while taking the characteristic data X as the main data and the characteristic data Z as secondary data.

Note that the cross correlation coefficients expressing the correlations are classified in stages by a plurality of reference levels. For example, values of the cross correlation coefficients are classified as being a level indicating a strong correlation in a range A7 (−1.0 to −0.7) and a range A1 (0.7 to 1.0). Further, for example, values of the cross correlation coefficients are classified as being a level indicating a correlation in a range A6 (−0.7 to −0.4) and a range A2 (0.4 to 0.7). Further, for example, values of the cross correlation coefficients are classified as being a level indicating a weak correlation in a range A5 (−0.4 to −0.2) and a range A3 (0.2 to 0.4). Further, for example, values of the cross correlation coefficients are classified as being a level indicating no correlation in a range A4 (−0.2 to 0.2). Note that the classification levels with respect to these cross correlation coefficients are one example, and levels of greater subdivision may be used.

Figure 17:
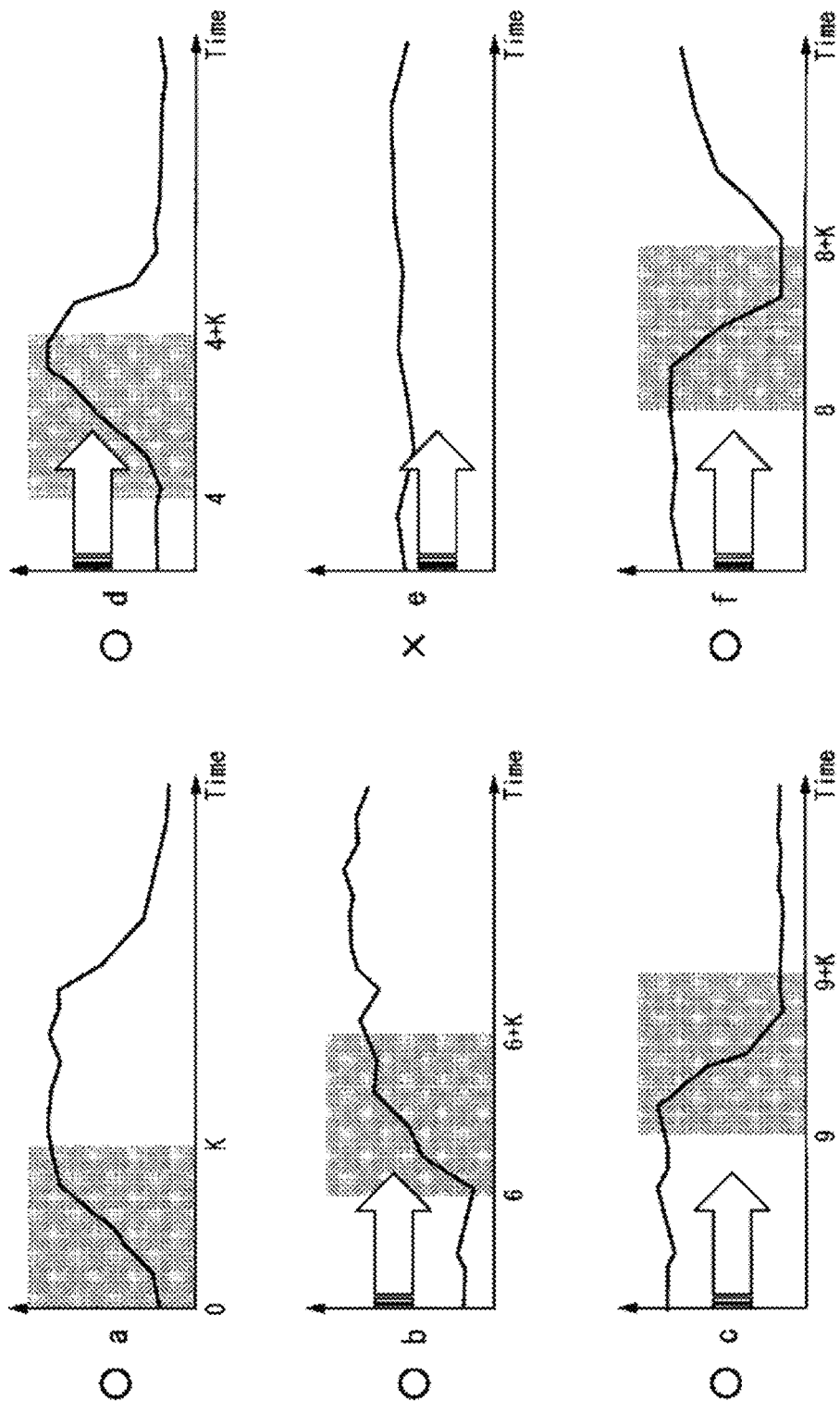

Here, a specific example of processing by the mechanism analysis unit 124 will be described with reference to FIGS. 17 to 22. FIG. 17 is a diagram illustrating an example of characteristic data indicating a strong correlation with respect to characteristic data a.

For example, taking a section (0 to k) of the characteristic data a as a reference, the mechanism analysis unit 124 identifies sections that indicate a strong correlation with respect to other characteristic data b to f. For example, in the characteristic data b, the mechanism analysis unit 124 identifies a section (6 to 6+k) that indicates a strong correlation with the section (0 to k) of the characteristic data a. Further, for example, in the characteristic data c, the mechanism analysis unit 124 identifies a section (9 to 9+k) that indicates a strong correlation with respect to the section (0 to k) of the characteristic data a. Further, for example, in the characteristic data d, the mechanism analysis unit 124 identifies a section (4 to 4+k) that indicates a strong correlation with respect to the section (0 to k) of the characteristic data a. Further, for example, in the characteristic data e, since there is no section indicating a strong correlation with the section (0 to k) of the characteristic data a, the mechanism analysis unit 124 does not identify a section indicating the strong correlation. Further, for example, in the characteristic data f, the mechanism analysis unit 124 identifies a section (8 to 8+k) that indicates a strong correlation with respect to the section (0 to k) of the characteristic data a.

From these results, of the characteristic data indicating the strong correlation, the mechanism analysis unit 124 assumes an order in which the characteristic data having the section with an earlier start time indicates a stronger correlation. On the basis of the assumed order, the mechanism analysis unit 124 calculates the correlations between the characteristic data. In other words, when the characteristic data a is taken as the main data, the mechanism analysis unit 124 calculates the correlations between the characteristic data in the order of the characteristic data d, b, f, and c.

Further, for example, taking a section (6 to 6+k) of the characteristic data b as a reference, the mechanism analysis unit 124 identifies sections that indicate a strong correlation with respect to the other characteristic data c to f. Hereinafter, the mechanism analysis unit 124 performs the same processing with respect to all of the characteristic data, and constructs a model representing the correlations between the characteristic data, of the characteristic data. A correspondence table of the correlations between all of the characteristic data constructed by the mechanism analysis unit 124 is illustrated in FIG. 18.

To verify the correlations between all of the characteristic data calculated by the mechanism analysis unit 124, a procedure is performed on the cells, by which changes in the characteristic quantity that is assumed to be a main characteristic quantity disappear, while other conditions are kept the same, and cells (a sample) are created. With respect to the cells after the procedure has been performed by which the changes in the characteristic quantity disappear, the observation device 1 captures images in time series, similarly to before the procedure is performed by which the changes in the characteristic quantity disappear, and acquires the same characteristic quantities as before the procedure is performed by which the changes in the characteristic quantity disappear.

Figure 19:
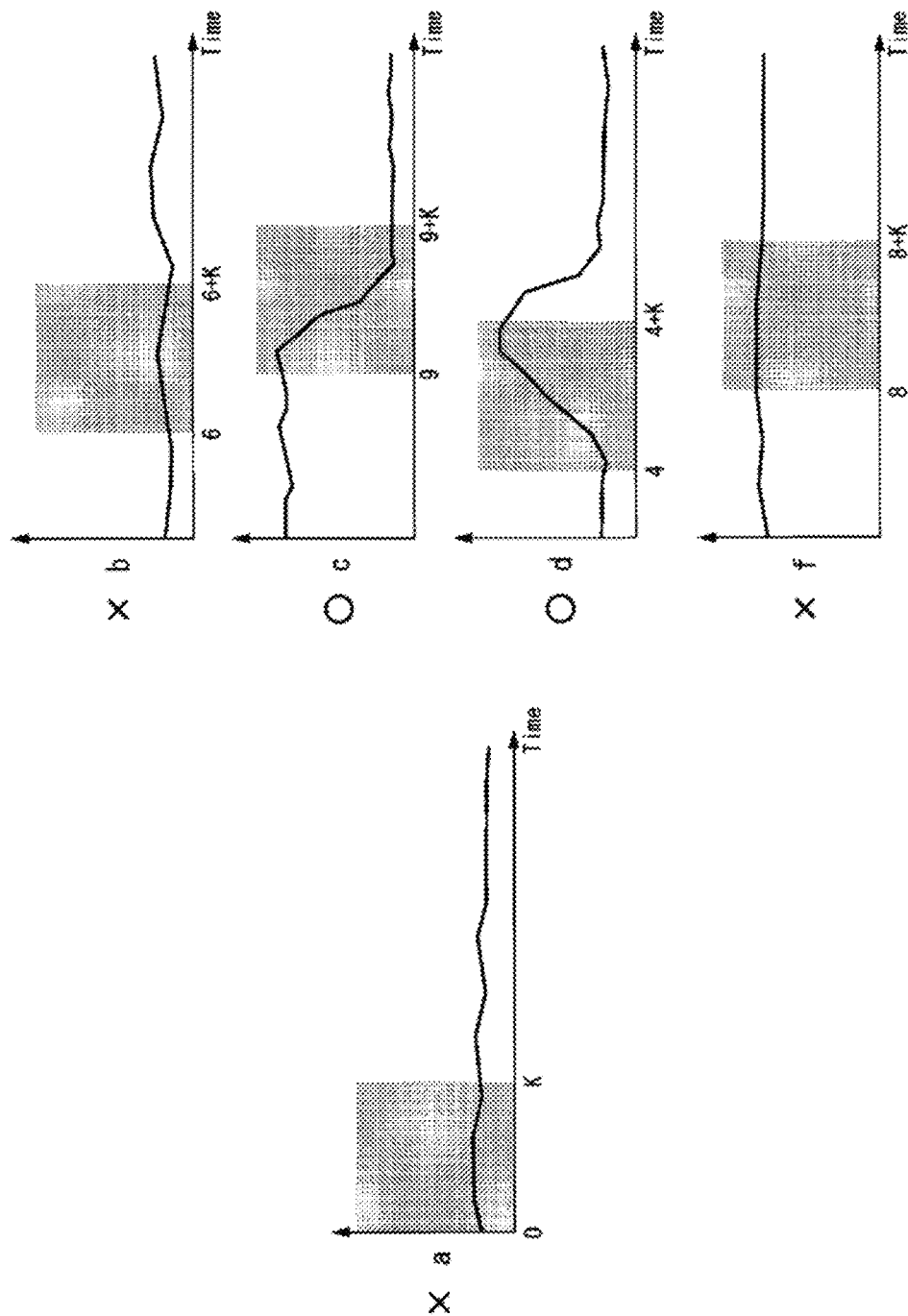
FIG. 19 is a diagram illustrating an example of characteristic data indicating a strong correlation with respect to characteristic data of cells to which an inhibitor has been added.
Figure 21:
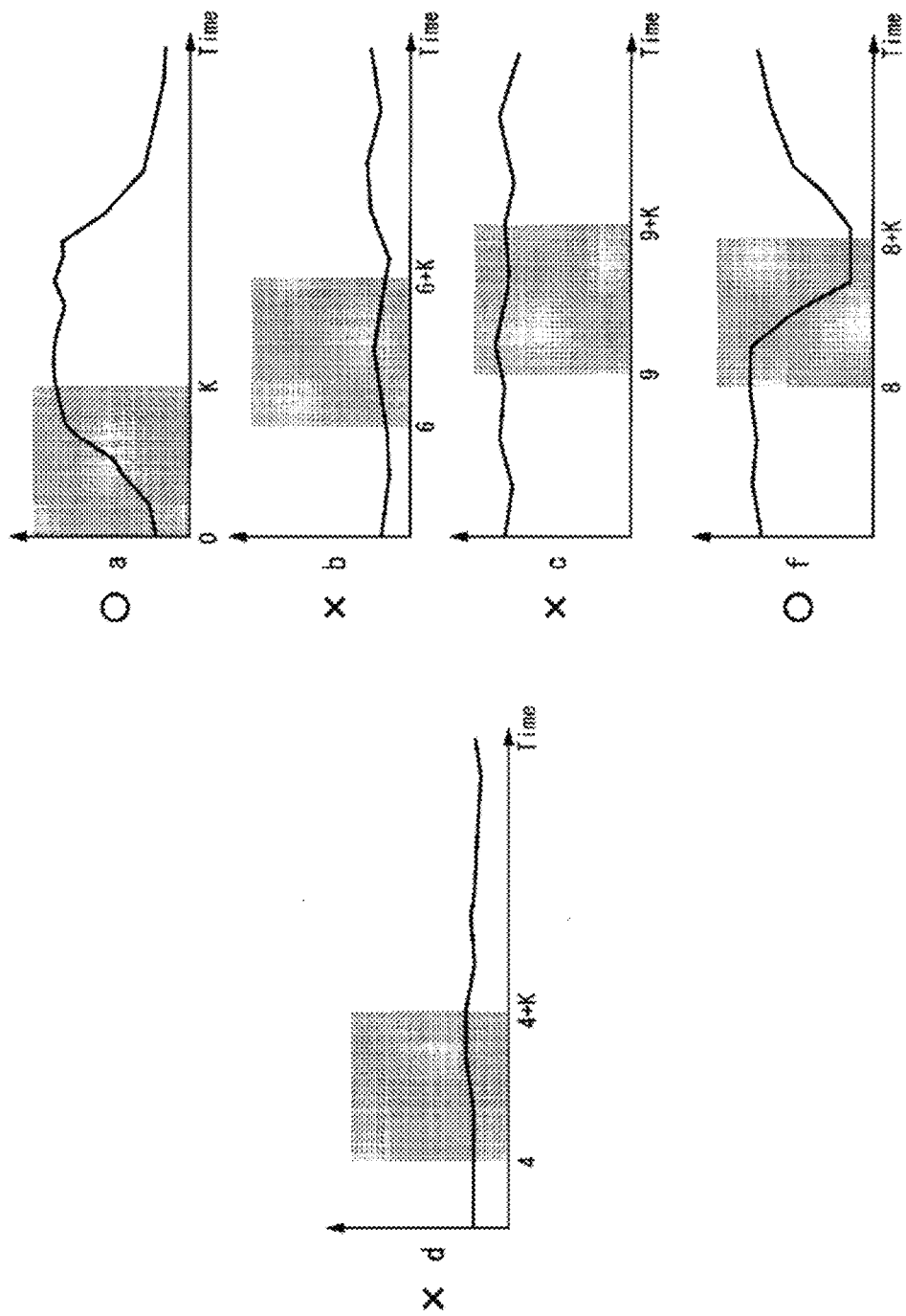
FIG. 21 is a diagram illustrating an example of characteristic data indicating a strong correlation with respect to characteristic data of cells on which a procedure has been performed by which a change in a characteristic quantity d disappears.

Next, calculation of a correlation between characteristic data of cells to which an inhibitor is added will be described with reference to FIGS. 19 to 21. FIG. 19 is a diagram illustrating an example of characteristic data indicating a strong correlation with respect to characteristic data of cells to which an inhibitor has been added. In the section (0 to k) of the characteristic data a, the changes in the characteristic quantity disappear due to the addition of the inhibitor.

For example, the mechanism analysis unit 124 calculates the correlations by comparing the characteristic data a of the cells to which the inhibitor has been added in the section (0 to k) with the other characteristic data b, c, d, and f in predetermined sections. The predetermined sections are the sections of the other characteristic data that indicate the strong correlation with respect to the characteristic data a before the inhibitor is added.

For example, the mechanism analysis unit 124 identifies the characteristic data b and f as the characteristic data indicating the strong correlation with respect to the characteristic data a of the cells on which the procedure has been performed by which changes in a characteristic quantity a disappear. Specifically, the mechanism analysis unit 124 identifies the characteristic data in which the changes in the characteristic quantity decrease as a result of a decrease in the change in the characteristic quantity of the characteristic data a. In this way, from the correlations between the characteristic data calculated before the procedure is performed by which the changes in the characteristic quantity a disappear, the mechanism analysis unit 124 newly calculates the correlations between the characteristic data while excluding the weak correlations. A correspondence table of the correlations between the characteristic data newly calculated by the mechanism analysis unit 124 is illustrated in FIG. 20.

Further, here, a procedure is newly performed on the cells by which changes in a characteristic quantity d disappear, while other conditions are kept the same, and cells (a sample) are created. With respect to the cells after the procedure is performed by which changes in the characteristic quantity d disappear, the observation device 1 captures images in time series, similarly to before the processing is performed by which the changes in the characteristic quantity d disappear, and acquires the same characteristic quantities as before the processing is performed by which the changes in the characteristic quantity d disappear.

On the basis of this characteristic quantity, the mechanism analysis unit 124 calculates the correlations between the characteristic data. FIG. 21 is a diagram illustrating an example of characteristic data indicating a strong correlation with respect to characteristic data of cells on which the procedure is performed by which the changes in the characteristic quantity d disappear. In the section (4 to 4 k) of the characteristic data d, the changes in the characteristic quantity disappear due to the performed procedure.

For example, the mechanism analysis unit 124 calculates the correlations by comparing the characteristic data d of the cells, on which the procedure has been performed by which changes in the characteristic quantity d in the section (4 to 4+k) disappear, with the other characteristic data a, b, c, and f in predetermined sections.

Figure 22:
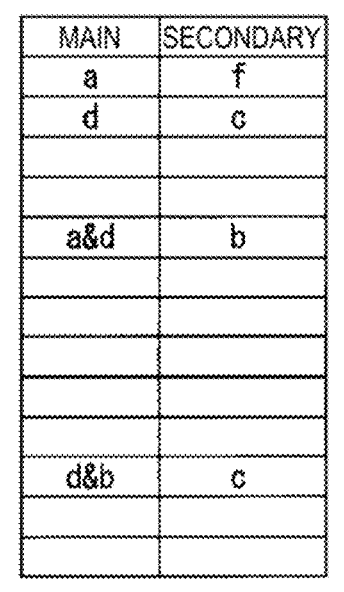

For example, the mechanism analysis unit 124 identifies the characteristic data b and c as the characteristic data indicating the strong correlation with respect to the characteristic data d of the cells on which the procedure has been performed by which the changes in the characteristic quantity d disappear. Specifically, the mechanism analysis unit 124 identifies the characteristic data in which the changes in the characteristic quantities decrease as a result of a decrease in the change in the characteristic quantities of the characteristic data d. In this way, from the correlations between the characteristic data calculated after the procedure has been performed by which the changes in the characteristic quantity a disappear and before the procedure is performed by which the changes in the characteristic quantity d disappear, the mechanism analysis unit 124 newly calculates the correlations between the characteristic data while excluding the weak correlations. A correspondence table of the correlations between the characteristic data newly calculated by the mechanism analysis unit 124 is illustrated in FIG. 22.

On the basis of the calculated correlations between the characteristic data, the mechanism analysis unit 124 calculates a correlation matrix. The correlation matrix is expressed by a combination of the characteristic data and an index (a cross correlation coefficient, for example) indicating a degree of the correlation calculated as a result of this combination. For example, the mechanism analysis unit 124 calculates a plurality of the correlation matrices so as to cover all patterns (variations) of combinations of the characteristic data.

Figure 23:
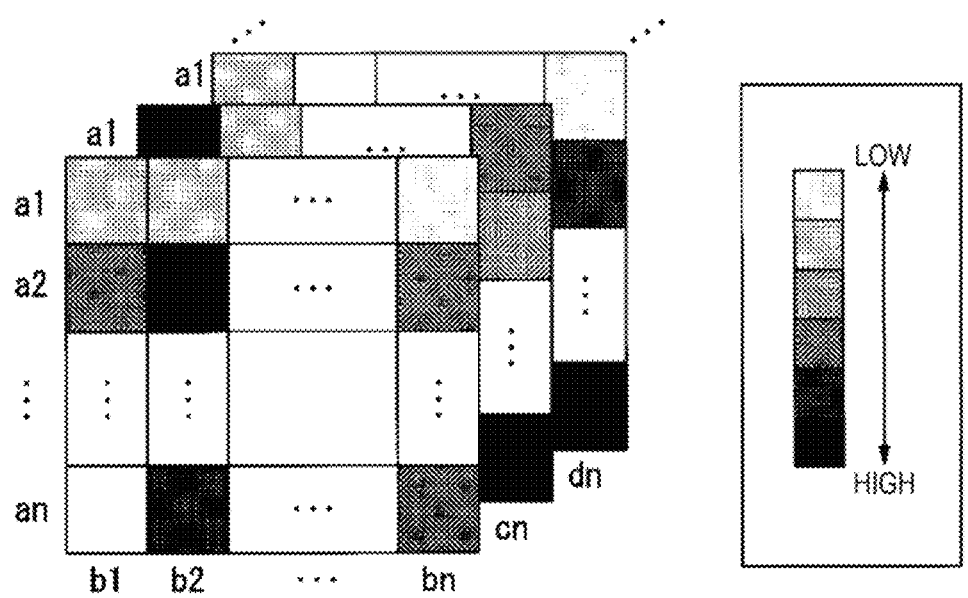
FIG. 23 is a diagram illustrating an example of correlation matrices.

FIG. 23 is a diagram illustrating an example of the correlation matrices. For example, in the present embodiment, from the element a, the characteristic data a1 to an are each created, and from the element b, the characteristic data b1 to bn are each created. A description of the further elements is omitted here.

Thus, for example, the mechanism analysis unit 124 expresses, as matrices, combinations of the various characteristic data a1 to an extracted from the element a and the various characteristic data b1 to bn extracted from the element b. The mechanism analysis unit 124 stores a numerical value of the correlation calculated on the basis of each of the characteristic data combinations in each component of these matrices. When the analysis device 100 submits the calculated correlation matrices to the user, each component is preferably represented using a color corresponding to the numerical value of the correlation.

From the calculated correlation matrices, the mechanism analysis unit 124 extracts the combinations of the characteristic data for which the correlation is high. For example, the mechanism analysis unit 124 calculates the number of components for which a value (the cross correlation coefficient or the like) indicating the correlation is higher than a predetermined value, and extracts, as the combinations of the characteristic data having a high correlation, the combinations for which the calculated number of components is high.

On the basis of the extracted combinations of the characteristic data having the high correlation, the mechanism analysis unit 124 constructs a model representing the correlations between the elements. Processing to construct the model representing the correlations between the elements will be described below.

Figure 24:
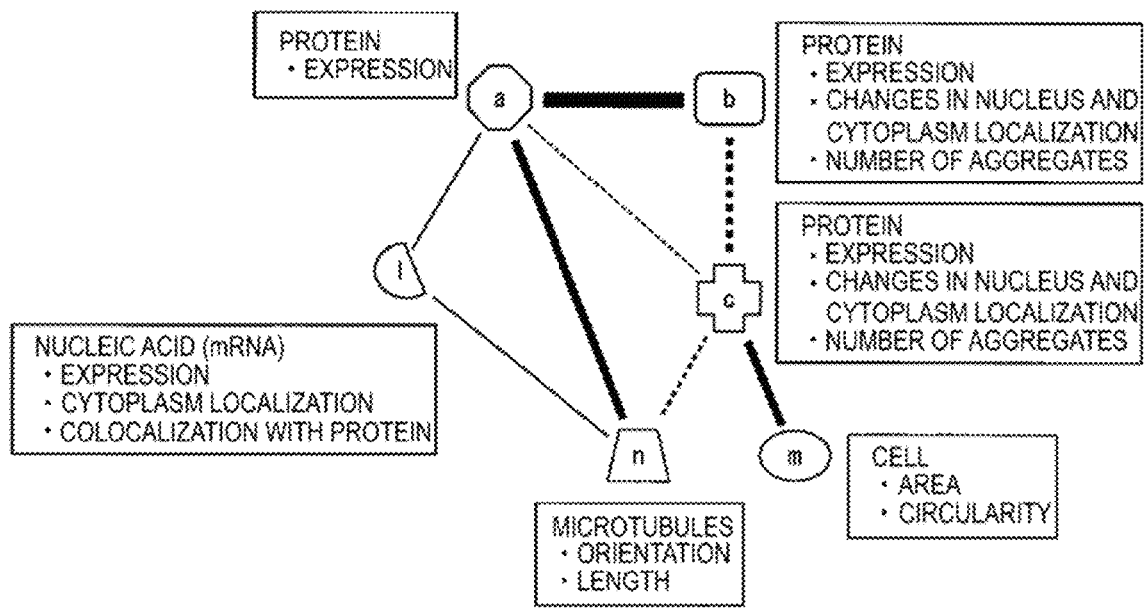
FIG. 24 is a diagram of a model representing correlations between elements.

FIG. 24 is a diagram of a model representing the correlations between the elements. The model of the illustrated example is, for example, constructed on the basis of correlation coefficients of each of combinations when combinations of the elements a and b, the elements a and n, the elements b and c, the elements c and n, and the element c and m have been extracted by the mechanism analysis unit 124 as the combinations having the high correlation. Note that a thickness of solid lines joining each of the elements illustrated in FIG. 24 represents strength of the correlation. Further, broken lines joining each of the elements indicate that the correlation between the elements has changed as a result of the procedure being performed by which the characteristic quantity of the element a disappears. In addition, the solid lines joining each of the elements indicate that the correlation between the elements does not change irrespective of whether or not the procedure is performed by which the characteristic quantity of the element a disappears.

As the characteristic data of the elements b and c, for example, the characteristic quantities of the expression of protein, localized changes between the nucleus and the cell, the number of aggregate bodies and the like are indicated. Further, as the characteristic data of an element l, for example, the characteristic quantities of an expression of nucleic acid (mRNA), cytoplasm localization, colocalization with a predetermined protein and the like are indicated. Further, as the characteristic data of the element n, for example, characteristic quantities of an arrangement, a length, and the like of an organelle are indicated. Further, as the characteristic data of the element m, for example, characteristic quantities of an area of the cell, a degree of circularity, and the like are indicated.

Here, for example, the procedure by which the changes in the element a disappear is performed on the cells that are the extraction source of the characteristic data illustrated in the model in FIG. 24. As a result, the mechanism analysis unit 124 can construct a model illustrating the new correlations between the elements. The model illustrating the correlations will be described below with reference to the drawings.

Figure 25:
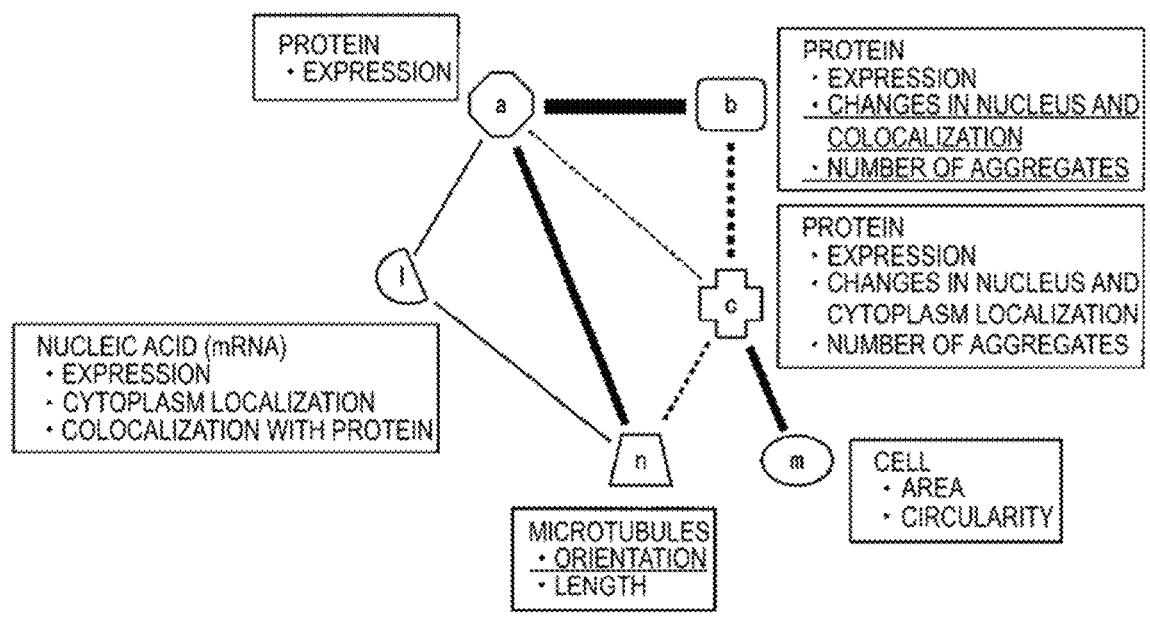
FIG. 25 is a diagram of a model indicating correlations between elements constructed after a procedure has been performed by which an expression, which is a characteristic quantity of an element a, disappears.

FIG. 25 is a diagram of a model illustrating correlations between the elements constructed after the procedure is performed by which the expression that is the characteristic quantity of the element a disappears. In FIG. 25, the underlined characteristic data (characteristic quantities) indicate the characteristic data (characteristic quantities) that change when the procedure is performed by which the expression that is one of the characteristic quantities of the element a disappears. Further, the characteristic data (characteristic quantities) that are not underlined indicate the characteristic data (characteristic quantities) that do not change when the procedure is performed by which the expression that is one of the characteristic quantities of the element a disappears.

In the illustrated example, the elements b and n are illustrated arranged in positions adjacent to the element a on a downstream side. This indicates that, after the procedure is performed by which the expression of the element a disappears, the characteristic quantities of the elements b and n have changed. In the case of this type of illustrated example, the mechanism analysis unit 124 performs the following processing.

When the characteristic data representing the expression of the element a has changed, the mechanism analysis unit 124 constructs a model in which the extraction source elements b and n, whose characteristic data change in accordance with that change, are arranged in the positions adjacent to the element a on the downstream side. As a result, the mechanism analysis unit 124 determines that the element a controls the elements b and n.

Further, in the illustrated example, the elements l, c, and m are illustrated arranged in positions that are not adjacent to the element a. This indicates that, after the procedure is performed by which the expression of the element a disappears, the characteristic quantities of the elements l, c, and m do not change. In this case, the mechanism analysis unit 124 performs the following processing.

When the characteristic data representing the expression of the element a has changed, the mechanism analysis unit 124 constructs the model in which the extraction source elements l, c, and m, whose characteristic data do not change in accordance with that change, are arranged in the positions that are not adjacent to the element a on the downstream side. As a result, the mechanism analysis unit 124 determines that the element a does not control the elements l, c, and m.

By performing the above-described processing with respect to the other elements, the mechanism analysis unit 124 can derive the following determination results in a similar manner.

The expression of the element b is not subject to the control of the element a
  Localization changes and aggregation of the element b are subject to the control of the element a
  An expression quantity of the element b is estimated to be controlling the element c
  An orientation of the element n is estimated to be linked with the element a
  An orientation of the element n is estimated to be linked with localization changes or aggregation of the element b Analysis II of Mechanisms At the same time as the processing by which the expression of the element a disappears, or after that processing, the mechanism analysis unit 124 performs the procedure by which those changes disappear for each of the other elements, and calculates the changes in the characteristic quantities of the other elements. By repeating this, the model representing the correlations between the elements is constructed. Specifically, on the basis of the calculated correlations between the characteristic data, the mechanism analysis unit 124 calculates the correlations between the analysis targets (the elements) and constructs the model representing the correlations between the elements. For the above-described correlation between the elements, a strength and direction of the correlations is expressed by a vector, for example. Hereinafter, this vector will be referred to as a "correlation vector."

Further, the correlation between the elements refers to a relationship in which fluctuations, maintenance, elimination, and expression of a given element influence fluctuations, maintenance, elimination, and expression of another element, or to a relationship in which fluctuations, maintenance, elimination, and expression of a given element influence the fluctuations, maintenance, elimination, and expression of the element itself. Note that these relationships are unidirectional, bidirectional or feedback relationships. Note that this type of model, for example, corresponds to a so-called signaling cascade or a signal network. Note also that the mechanism analysis unit 124 may perform not only the procedure by which the changes in the characteristic quantity disappear, and may also perform a procedure by which changes in the other characteristic quantities disappear, and thereby calculate the correlations between the elements. Further, the correlations (the signaling cascade, for example) between the elements are not limited to reactions of chemical substances, such as gene expression, the activation of proteins or the creation of metabolites, and may be a cascade reaction of the elements covering vital phenomena in general, including reactions of cells, such as the activation of organelles, the directionality of microfilaments, cell death, and the cell cycle.

Figure 26:
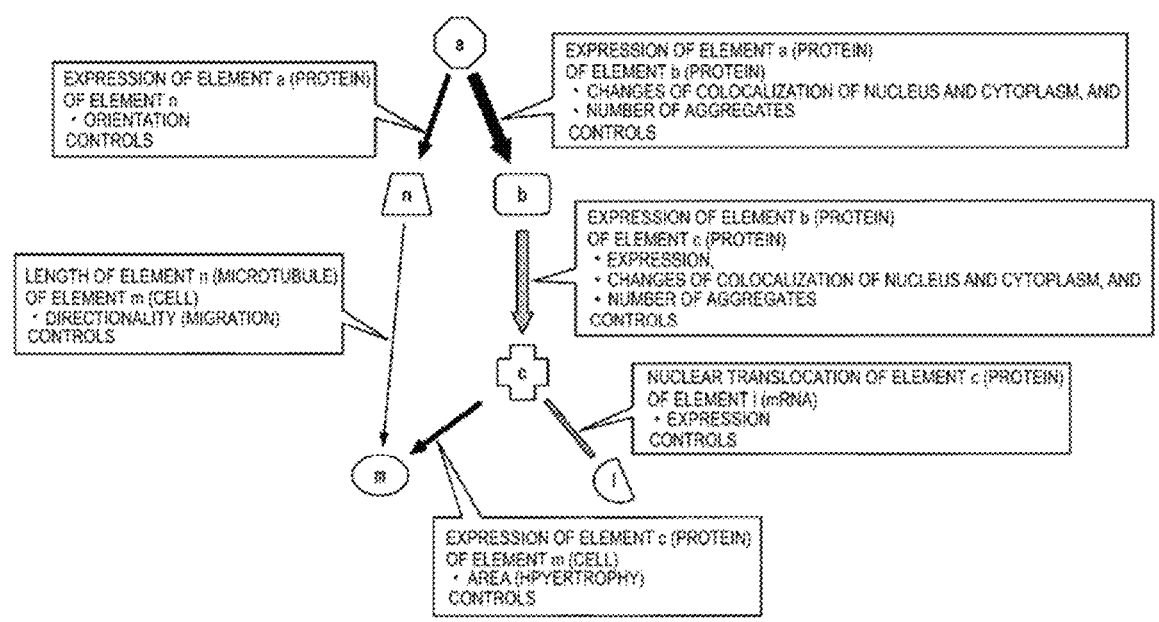
FIG. 26 is a diagram of a model illustrating correlations between elements.

FIG. 26 is a diagram of a model representing the correlations between the elements. The arrows in FIG. 26 represent the correlation vectors. Therefore, a thickness of the arrow indicates the strength of the correlation, and a direction of the arrow indicates a direction of the correlation. For example, when taking the element a as the main element, the mechanism analysis unit 124 constructs a model, taking the element a as a base point, representing the correlations between the elements such that the element having the strongest correlation with the element a becomes the next stage of the cascade. As illustrated in FIG. 26, on the basis of the calculated correlations between the characteristic data, the mechanism analysis unit 124 constructs the model in which the elements n and b are the next stage of the base point.

In the illustrated example, the analysis device 100 can estimate the following. At the same time as controlling the orientation of the element n (microtubules), the element a controls localization changes between the nucleus and the cell, the number of aggregates, and the like of the element b (protein). Further, a length of the element n (the microtubules) controls the directionality (migration) of the element m (cell). Further, the expression of the element b (a protein) controls the expression, localization changes between the nucleus and the cell, the number of aggregates, and the like of the element c (a protein). In addition, nuclear translocation of the element c (the protein) updates the expression of the element l (nucleic acid mRNA). Further, the expression of the element c (the protein) invites hypertrophy of the element m (the cell).

With the analysis device 100, until the model representing the correlations between the elements calculated by the mechanism analysis unit 124 indicates a predetermined relationship, the user newly creates the cells on which are performed the procedure by which the changes in the specific characteristic qualities disappear, or the procedure by which changes in a combination of a plurality of characteristic qualities disappear, and repeats the above-described processing. The predetermined relationship is, for example, the establishment of the directionality of the correlation vector. Specifically, taking an analysis target X, which is the extraction source of the characteristic data X, as the main analysis target and an analysis target Y, which is the extraction source of the characteristic data Y, as the secondary target, the mechanism analysis unit 124 calculates a model illustrating the correlations between the elements. In this way, the cell desired by the user can be produced.

Analysis III of Mechanisms

Further, on the basis of the cross correlation coefficients between the characteristic data, the mechanism analysis unit 124 may perform grouping of each of the elements close to a predetermined characteristic quantity, and may calculate the correlations between the grouped elements. Processing to perform the grouping for each of elements will be described below. Further, in the following description, the "cell" is described as the example of the element, but it may be another element configuring the mechanism that controls vital phenomena.

For example, the mechanism analysis unit 124 calculates the cross correlation coefficients as the values indicating the correlations for each of the cells separated by the cell region separation unit 118. For example, with respect to a cell 1 separated by the cell region separation unit 118, the mechanism analysis unit 124 calculates the cross correlation coefficients of each of the elements a to f configuring the cell 1.

An example of the cross correlation coefficients calculated by the mechanism analysis unit 124 is illustrated in FIG. 27. For example, the mechanism analysis unit 124 calculates a cross correlation coefficient of 0.85 from the element a to the element b.

On the basis of the calculated cross correlation coefficients for each of the cells, the mechanism analysis unit 124 performs the grouping for each of the cells close to the predetermined characteristic quantity. The predetermined characteristic quantity is, for example, a quantity indicating a distance between the cells that exceed a constant threshold value, on coordinates of an n-dimensional vector space illustrating influences between the elements. Note that the predetermined characteristic quantity may be calculated in advance by experimentation or the like, and may be stored in the storage unit 130 or the like.

Figure 28:
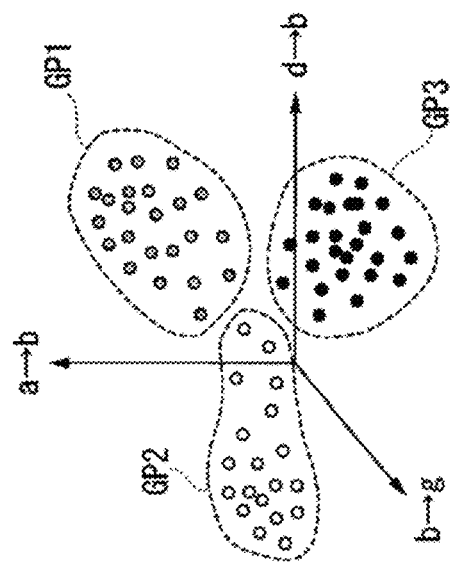
FIG. 28 is a schematic diagram of an example illustrating processing to group cells.
Figure 28:
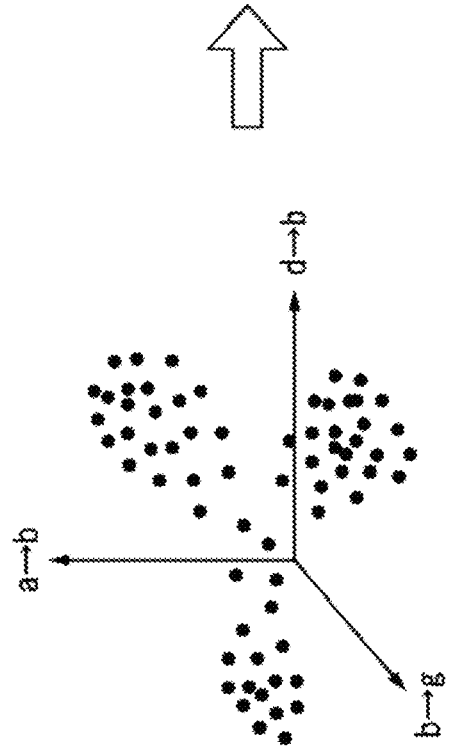

FIG. 28 is a schematic diagram of an example illustrating processing to perform the grouping of the cells. The mechanism analysis unit 124 causes the cells to be distributed on n-dimensional coordinates, where a number indicating the influences between the elements is a dimensionality n. With respect to the cells distributed on the n-dimensional coordinates, the mechanism analysis unit 124 performs clustering processing on the basis of the predetermined characteristic quantity, and groups the cells. For example, the mechanism analysis unit 124 causes the cells to be distributed on the n-dimensional coordinates on the basis of the influence from the element a in the direction of the element b, the influence from the element b in the direction of the element g, and the influence from the element d in the direction of the element b. By the clustering processing of the cells distributed on the n-dimensional coordinates, the mechanism analysis unit 124 classifies the cells into three groups (GP1 to GP3), for example.

Next, on the basis of the cross correlation coefficients of the grouped cells, the mechanism analysis unit 124 constructs and analyzes a model (a signaling cascade, for example) representing the correlations between the elements.

Figure 29:
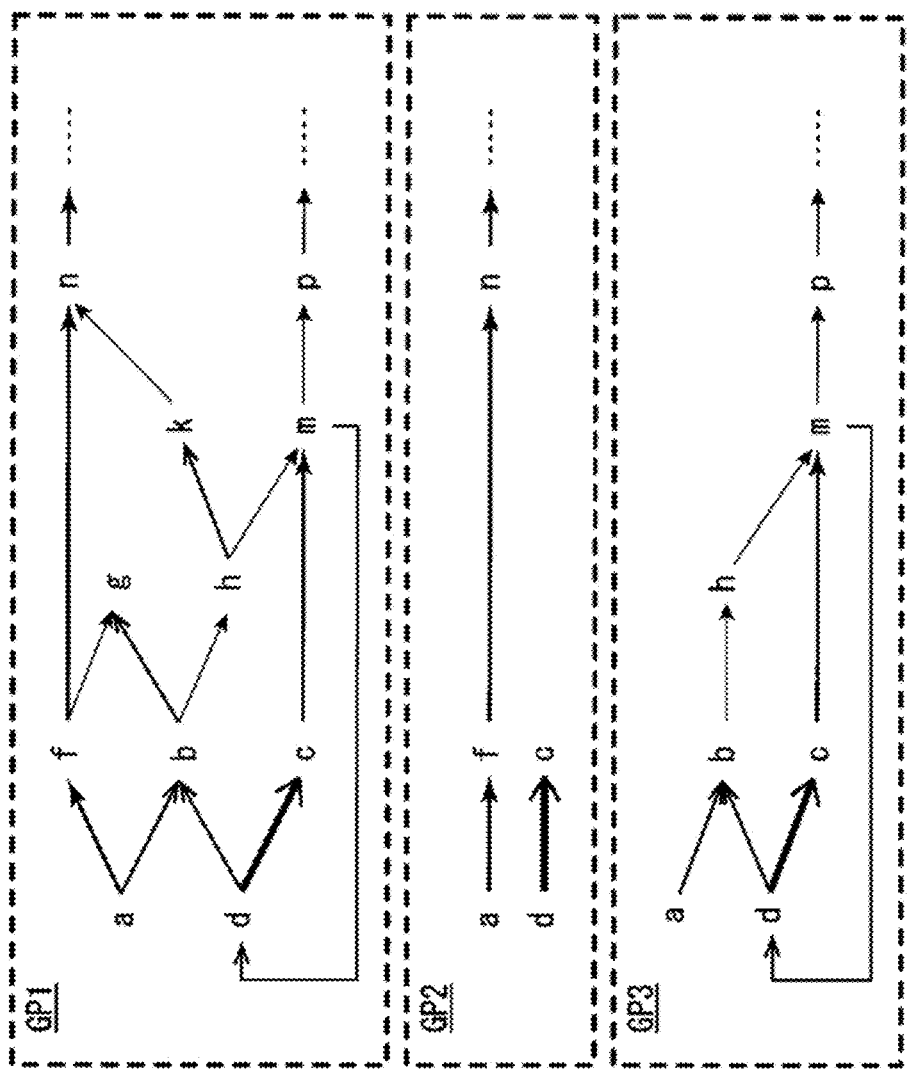
FIG. 29 is a diagram illustrating an example of models of signaling cascades constructed for each group by the mechanism analysis unit 124.

FIG. 29 is a diagram illustrating an example of models of signaling cascades constructed for each group by the mechanism analysis unit 124. For example, the mechanism analysis unit 124 constructs a model of a signaling cascade for each of the three classified groups (GP1 to GP3).

In this way, in the case of cells configured by a plurality of cells in which signaling cascades of different analysis targets are activated, or by cells for which a degree of activation is different even within the same signaling cascade, spatiotemporal characteristics of an activated state of these cells can be analyzed.

Figure 30:
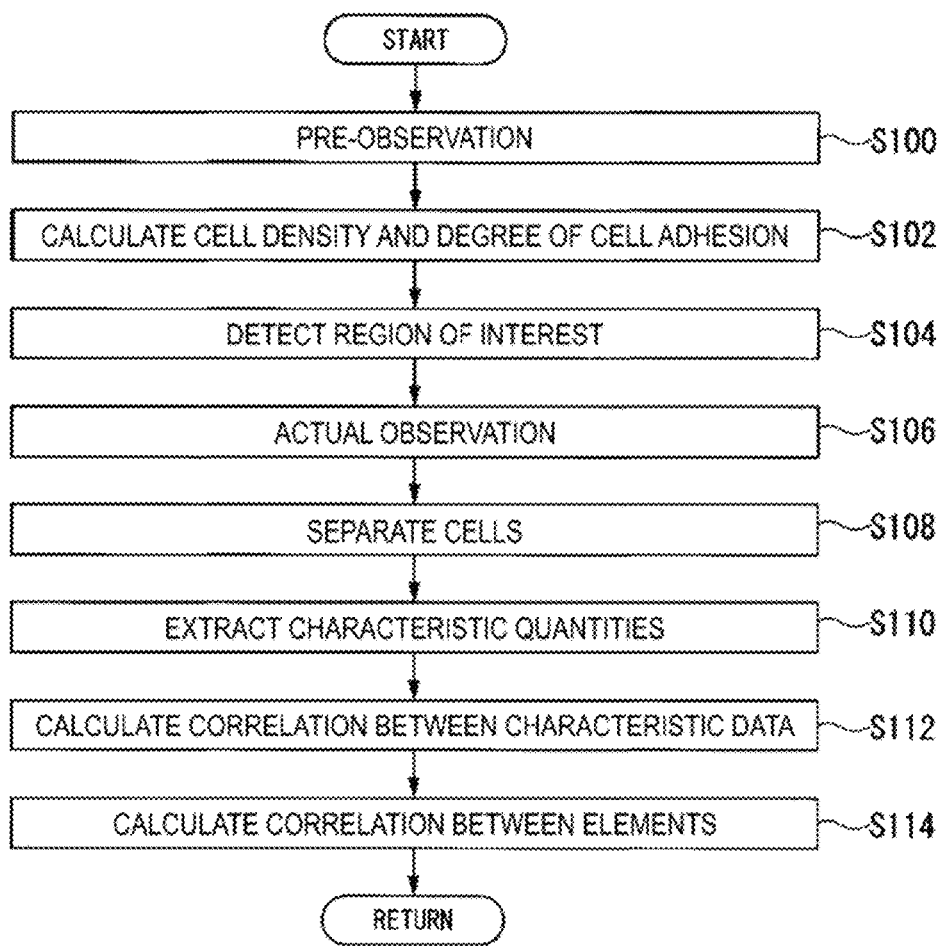
FIG. 30 is a flowchart of a flow of processing performed by the analysis device 100.

FIG. 30 is a flowchart illustrating a flow of processing performed by the analysis device 100. The analysis device 100 repeatedly performs the processing of this flowchart, for example, the number of times freely-selected by the user.

First, as the pre-observation, the microscope control unit 112 controls the microscope 200 so as to capture the image of the whole of the culture vessel at the low magnification (wide range), and acquires the low resolution image (step S100). Alternatively, the microscope control unit 112 may control the microscope 200 so as to perform the tiling image capture of the whole of the culture vessel at a medium magnification. The density calculation unit 114 calculates the cell density and the degree of cell adhesion of the cells "cell" present in the region F representing the whole image of the culture vessel, in the image obtained by the microscope 200 (step S102). Next, on the basis of the cell density and the degree of cell adhesion calculated by the density calculation unit 114, the region of interest detection unit 116 detects the region of interest R (step S104).

Next, as the actual observation, the microscope control unit 112 controls the microscope 200 so as to capture the image of the region of interest R at a high magnification, and acquires the high resolution image (step S106). Next, on the high resolution image captured by the microscope 200, the cell region separation unit 118 detects the cell regions and separates the cells (step S108). Next, from the image on which the cells are separated by the cell region separation unit 118, the characteristic quantity extraction unit 122 extracts the various characteristic quantities, such as substances passing between the cells or moving intracellularly, gene expression, the activation of organelles, the directionality of the elements inside the cells, and reactions of the cells such as the cell cycle (step S110).

Next, on the basis of the time series extracted by the characteristic quantity extraction unit 122, changes in a growth environment of the cells, or the characteristic data and spatial sequence characteristic data resulting from changes in the state of the cell itself, the mechanism analysis unit 124 calculates the correlations between the characteristic quantity data (step S112). Next, on the basis of the calculated correlations between the characteristic quantity data, the mechanism analysis unit 124 calculates the correlations between the elements that are the extraction source of the characteristic data (step S114). In this way, the present flowchart ends.

Other Processing of Mechanism Analysis Unit 124

Figure 31:
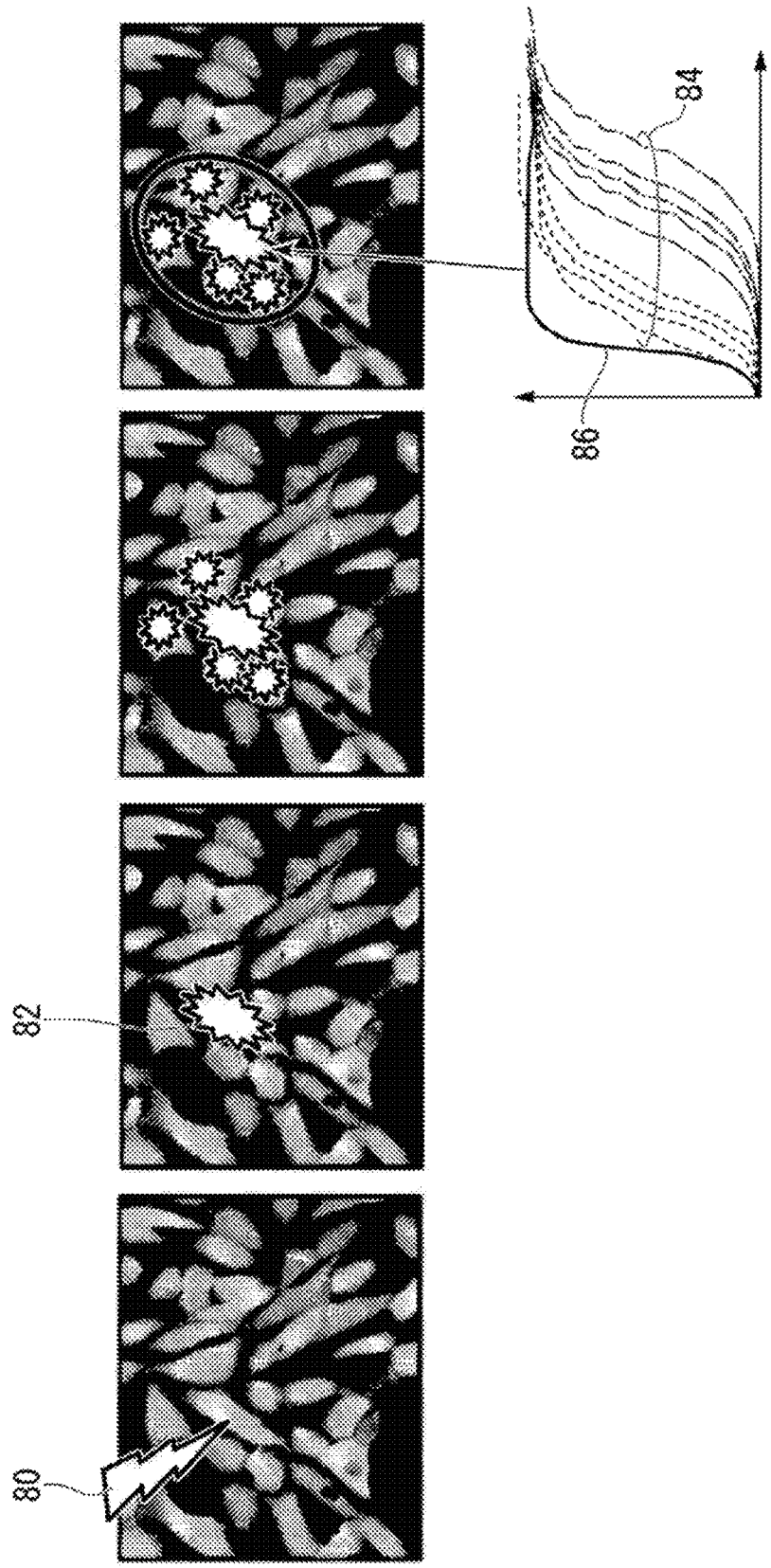
FIG. 31 is a diagram illustrating an example of a manner in which a stimulus signal spreads between cells.

The mechanism analysis unit 124 may calculate the correlations between the elements on the basis of various characteristic data extracted in spatial sequence by the characteristic quantity extraction unit 122. FIG. 31 is a diagram illustrating an example illustrating a manner of a stimulus signal spreading between cells. As illustrated in FIG. 31, for example, with the mechanism analysis unit 124, when a stimulus 80 is introduced from outside into the culture vessel, in accordance with this stimulus 80, signals are transmitted from a cell 82 to the surrounding cells. As a result, the stimulus introduced into the culture vessel acts as a trigger, and the mechanism analysis unit 124 can identify a signal network group activated in the surrounding cells. As a result, the analysis device 100 can analyze a spatiotemporal timing of the activation of the signal network group, by measuring the characteristic quantities identifying the activated signal network group for each of the cells and measuring the spatiotemporal timing at which those characteristic quantities are expressed.

Further the mechanism analysis unit 124 may analyze the spatiotemporal timing at which the signal network group(s) is activated by combining characteristic data 84 extracted in spatial sequence with characteristic data 86 extracted in time series.

Alternatively, the mechanism analysis unit 124 may construct relationships in which the cell to which the stimulus is introduced is the main cell and the cells to which the stimulus is not introduced are the secondary cells. In this way, of the characteristic data that are extracted from the cells to which the stimulus is not introduced and that represent the correlations, the mechanism analysis unit 124 can assume an order from those having a stronger correlation. On the basis of the assumed order of the characteristic data, the mechanism analysis unit 124 constructs a model representing the correlations between the elements. Specifically, on the basis of distances between the elements, the mechanism analysis unit 124 calculates the correlations between the elements, and on the basis of a magnitude of each of the calculated correlations between the elements, constructs the model representing the correlations between the elements.

Observation Support System

When performing the image capture of the analysis target, the analysis device 100 may acquire optimum imaging conditions (Optical Configuration: OC) from the external storage device 300, and may perform related processing on the basis of the acquired optimum imaging conditions OC. The optimum imaging conditions OC include parameters, such as a magnification of the microscope 200 and a sensitivity of a focal position detector that are associated with the analysis target, exposure conditions, a resolution of the detector, a strength of transmitted light, a strength and wavelength of fluorescent excitation light, auto focus conditions, and selection of a filter for fluorescence imaging. Note that the optimum imaging conditions OC are assumed to be acquired in advance by the analysis device 100, another analysis device or the like, and stored in a storage device, such as the external storage device 300.

Figure 32:
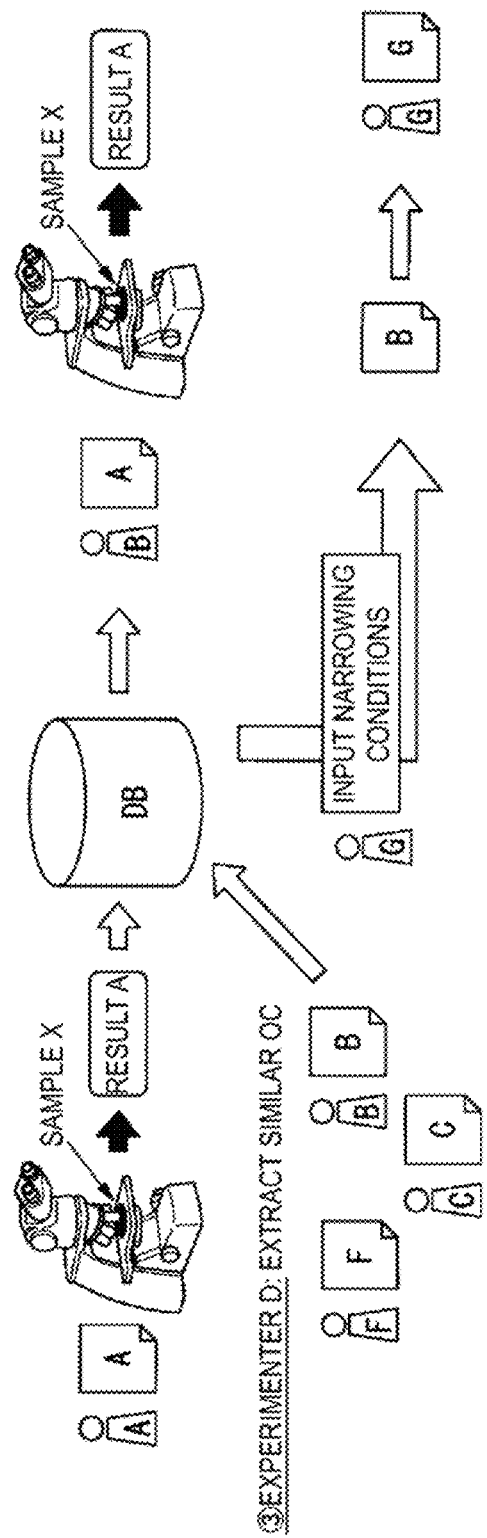
FIG. 32 is a diagram illustrating an example of processing performed on the basis of optimum imaging conditions OC.

FIG. 32 is a diagram illustrating an example of processing performed on the basis of the optimum imaging conditions OC. Depending on the analysis target, the analysis device 100 acquires optimum imaging conditions OC matching or similar to that of the analysis target from the external storage device 300. The analysis device 100 performs the related processing on the basis of the optimum imaging conditions OC acquired from the external storage device 300. When the analysis device 100 changes some of the optimum imaging conditions OC acquired from the external storage device 300 and captures the image of the analysis target, the analysis device 100 stores the new optimum imaging conditions OC to which those changes have been added in the external storage device 300. In this way, in the image capture of the analysis target, the setting of the conditions (parameters) can be reduced. Further, reproducibility of experiments relating to the analysis can be improved.

Figure 33:
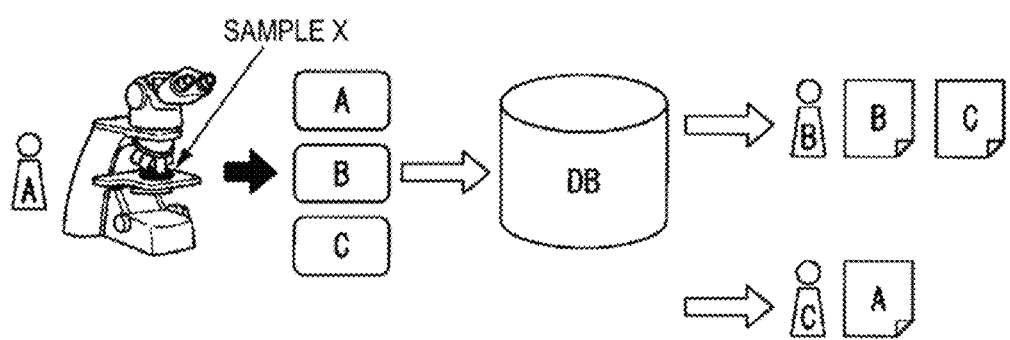
FIG. 33 is a diagram illustrating an example of processing to acquire an image associated in advance with other information.

In addition, the analysis device 100 may acquire an image associated in advance with other information, from a storage device such as the external storage device 300. FIG. 33 is a diagram illustrating an example of processing to acquire an image associated in advance with other information. For example, the analysis device 100 associates, in advance, an image with other information, and stores this in the storage device such as the external storage device 300. The other information includes, for example, various pieces of information relating to analysis, such as a wavelength, a name of the analysis target, a type of cell, a project name, and experiment conditions. For example, the user can acquire, from the external storage device 300, via the analysis device 100, an image relating to a protein that is the name of the analysis target. Further, for example, the user can acquire, from the external storage device 300, via the analysis device 100, an image relating to a predetermined dye color that is an experiment condition. In this way, it is possible to adapt to a mode of use of the user, and convenience can be improved.

Image Capture Region Specification System

Figure 34:
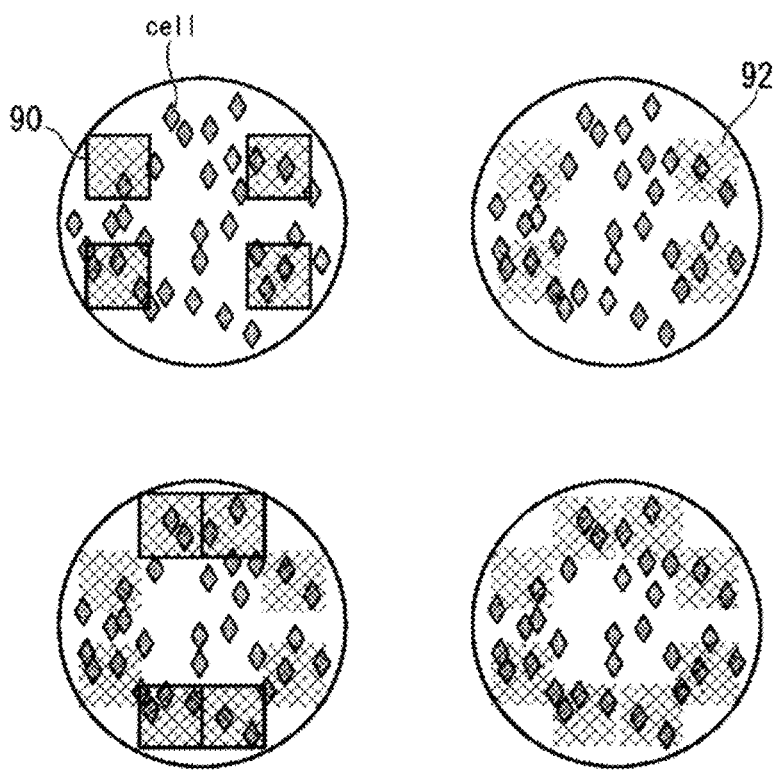
FIG. 34 is a diagram illustrating an example of processing to select a next image capturing position, on the basis of acquired image capture information.

When performing image capture of the culture vessel a plurality of times, the analysis device 100 may acquire information about a previous image capture position from the storage unit 130, and may select a next image capture position on the basis of the acquired previous image capture position information. The image capture position is a position at which the image capture has already been performed in the culture vessel. FIG. 34 is a diagram illustrating an example of processing to select the next image capture position, on the basis of acquired image capture information.

As illustrated in FIG. 34, when a previous image capture position 92 is the same position with respect to a next image capture position 90, for example, the analysis device 100 selects the next image capture position while avoiding the previous image capture position 92. In this way, the influence of phototoxicity resulting from the irradiation of light at the time of image capture, decoloration of fluorescent light and the like can be suppressed. This is also useful when evaluating the strength of light, evaluating cytotoxicity, and the like.

According to the analysis device 100 of the above-described embodiment, the images of the cells are acquired, and the elements configuring the mechanisms controlling vital phenomena are identified on the basis of the acquired images of the cells, characteristic data representing characteristic quantities of the elements are calculated for each of the identified elements, and the correlations between the characteristic data are calculated on the basis of the calculated characteristic data. The correlations between the elements are calculated on the basis of the calculated correlations between the characteristic data. In this way, the analysis device 100 can analyze the relationships between the elements configuring the mechanisms controlling the vital phenomena relating to the cells, while performing the appropriate analysis of the images.

Further, according to the analysis device 100 of the present embodiment, by performing the analysis of the identifiable elements on the basis of the acquired images of the cells, it is possible to calculate the correlations between the elements whereby the mechanisms controlling the vital phenomena are reflected with a high degree of reliability. Further, according to the analysis device 100 of the present embodiment, by performing the analysis of the identifiable elements on the basis of the acquired images of the cells, it is possible to calculate the correlations having a high degree of reliability, even in the case of correlations between the elements of different types.

In addition, according to the mechanism analysis unit 124 of the embodiment, by constructing the respective models of the signaling cascades as the models representing the correlations between the elements, with respect to the sorted groups, even in the case of the cells configured by the plurality of cells in which different signaling cascades are activated, the model of the compatible signaling cascade can be constructed.

Furthermore, according to the mechanism analysis unit 124 of the embodiment, by combining the characteristic data extracted in the spatial sequence and the characteristic data extracted in the time series, a state of transmission of signals between the cells with respect to a stimulus, an influence of contact between the cells, and the like can also be analyzed.

In addition, according to the analysis method of the embodiment, the analysis processing can be repeatedly performed until the model representing the correlations between the elements constructed by the mechanism analysis unit 124 indicates the predetermined relationship.

In addition, according to the analysis method of the embodiment, by repeatedly performing the analysis processing until the model representing the correlations between the elements constructed by the mechanism analysis unit 124 indicates the predetermined relationship, the cells desired by the user can be created.

Note that the microscope 200 of the above-described embodiment is an example of an "acquisition unit," the density calculation unit 114, the region of interest detection unit 116, and the cell region separation unit 118 are an example of an "identification unit," and the characteristic quantity extraction unit 122 and the mechanism analysis unit 124 are an example of a "calculation unit." Note also that the processing of the characteristic quantity extraction unit 122 and the mechanism analysis unit 124 may be performed by only one of either of the functional units. Further, the processing of the characteristic quantity extraction unit 122 and the mechanism analysis unit 124 may be performed by another functional unit, such as the density calculation unit 114, the region of interest detection unit 116, or the cell region separation unit 118. Another embodiment (a modified example) will be described below.

The above-described various processing steps may be realized by recording a program for executing these processing steps of the analysis device 100 in a recording medium that can be read by a computer and causing a computer system to read and execute the program recorded in the recoding medium.

Note that the "computer system" referred to here includes an OS and hardware such as a peripheral device. Further, when the "computer system" uses a WWW system, this includes a homepage provision environment (or display environment). Moreover, a "recording medium that can be read by a computer" refers to a portable recording medium such as a flexible disk, a magneto-optical disk, a ROM, a writable non-volatile memory such as a flash memory, or a CD-ROM, or a storage device such as a hard disk that is built into the computer system.

Further, the "recording medium that can be read by a computer" may also include a medium that holds the program for a certain period of time, such as a volatile memory (a DRAM, for example) built into a computer system that is a server or a client when the program is transmitted over a network such as the Internet or a communication line such as a phone line. In addition, the above-described program may be transmitted, from the computer system in which the program is stored in a storage device or the like, to another computer system, via a transmission medium or by transmission waves in the transmission medium. Here, the "transmission medium" that transmits the program refers to a medium having a function to transmit information, such as the Internet or another network (communication network), and a communication line such as a telephone line. Further, the above-described program may be a program for realizing a part of the above-described functions. Moreover, the above-described functions may be realized by a combination of this program with a program already recorded in the computer system, namely, by a so-called differential file (differential program).

Above, the embodiments of the present invention are described in detail with reference to the drawings, but a specific configuration is not limited to the embodiments, and designs and the like within the scope of the present invention are included.

The invention claimed is:

1. A determination device determining a correlation between a plurality of elements in a cell from a cell image, the cell image including an image of the cell to which a stimulus is applied, the plurality of elements in the cell including at least one of the cell and a substance that configures the cell, the determination device comprising:
   a processor programmed to:
      detect different regions in the cell image comprising a cell region, a nucleus region, a cytoplasm region, and a nuclear membrane region;
      extract changes in characteristic quantities of each of the plurality of elements in the cell from the cell image, the characteristic quantities comprising at least one or more statistics of luminance values in each of the cell region, the nucleus region, the cytoplasm region, and the nuclear membrane region;
      calculate a first correlation between a first element and a second element different from the first element among the plurality of elements in the cell, the first correlation being calculated based on a correlation between an extracted change in characteristic quantity of the first element and an extracted change in characteristic quantity of the second element;
      calculate a second correlation between a third element and a fourth element different from the third element among the plurality of elements in the cell, the second correlation being different from the first correlation and being calculated based on a correlation between an extracted change in characteristic quantity of the third element and an extracted change in characteristic quantity of the fourth element, each correlation being calculated as a cross-correlation between the extracted changes, each cross-correlation defining a strength of the correlation between the respective characteristic quantities; and
      compare strength of the calculated first correlation with strength of the calculated second correlation.

2. The determination device according to claim 1, wherein a thickness of a first line representing the first correlation and a thickness of a second line representing the second correlation are changed and illustrated based on the strength of the first correlation and the strength of the second correlation.

3. The determination device according to claim 1, wherein the strength of the first correlation and the strength of the second correlation are divided into a plurality of levels.

4. The determination device according to claim 1, wherein a new correlation is extracted according to strength of a respective correlation between the plurality of elements.

5. The determination device according to claim 1, wherein each of the plurality of elements includes at least one of the cell and a substance present inside the cell and configuring the cell.

6. The determination device according to claim 5, wherein the substance includes at least one of a cell organelle and a biological material of the cell.

7. The determination device according to claim 1, wherein each of the plurality of elements includes at least one of
(i) a substance identifiable based on contrast information of the cell image and (ii) a phenomenon identifiable based on contrast information of the cell image.

8. The determination device according to claim 1, wherein the processor is programmed to:
extract an expression of the plurality of elements present inside the cell as each of the characteristic quantities of the plurality of elements.

9. The determination device according to claim 1, wherein the processor is programmed to:
extract a distribution of shapes or a distribution of positions of the plurality of elements present inside the cell as each of the characteristic quantities of the plurality of elements.

10. The determination device according to claim 9, wherein the processor is programmed to:
extract a distribution of shapes of elements present inside a nucleus of the cell as each of the characteristic quantities of the plurality of elements.

11. The determination device according to claim 1, wherein the processor is programmed to:
extract a directionality of the plurality of elements present inside the cell as each of the characteristic quantities of the plurality of elements.

12. The determination device according to claim 1, wherein the processor is programmed to:
extract a state of the cell as each of the characteristic quantities of the plurality of elements.

13. The determination device according to claim 12, wherein
the state of the cell is a state including a cell death and a cell cycle.

14. The determination device according to claim 1, wherein the processor is programmed to:
extract a movement of the plurality of elements present inside the cell as each of the characteristic quantities of the plurality of elements.

15. The determination device according to claim 1, wherein the processor is programmed to:
extract co-localization of positions of the plurality of elements present inside the cell as each of the characteristic quantities of the plurality of elements.

16. The determination device according to claim 1, wherein the processor is programmed to:
extract a domain of the plurality of elements present inside the cell as each of the characteristic quantities of the plurality of elements.

17. The determination device according to claim 1, wherein the processor is programmed to:
calculate an initial correlation between a characteristic quantity of a respective one of the plurality of elements and a characteristic quantity of another respective one of the plurality of elements; and
calculate a correlation between the respective element and the other respective element based on the calculated initial correlation.

18. The determination device according to claim 17, wherein the processor is programmed to:
calculate a correlation vector representing the correlation between the respective element and the other respective element based on the calculated initial correlation.

19. The determination device according to claim 17, wherein the processor is programmed to:
calculate a matrix representing the initial correlation between the characteristic quantity of the respective element and the characteristic quantity of the other respective element.

20. The determination device according to claim 17, wherein the processor is programmed to:
extract first characteristic quantities of the respective element and the other respective element in spatial sequence based on positions and an arrangement of the respective element and the other respective element in the cell image;
extract second characteristic quantities of the respective element and the other respective element in time series from a plurality of cell images acquired in time series; and
calculate the correlation between the respective element and the other respective element by combining the first characteristic quantities in the spatial sequence with the second characteristic quantities in the time series.

21. The determination device according to claim 17, wherein the processor is programmed to:
calculate the initial correlation between the characteristic quantity of the respective element and the characteristic quantity of the other respective element while changing at least one of a time, a degree of change in a growth environment of the cell, and a degree of change in a state of the cell.

22. The determination device according to claim 21, wherein the processor is programmed to:
calculate the correlation between the respective element and the other respective element based on a direction in which the time, the degree of change in the growth environment of the cell, and the degree of change in the state of the cell are changed when the initial correlation is largest.

23. The determination device according to claim 17, wherein the processor is programmed to:
group the plurality of elements by calculating a value representing a cross correlation between the characteristic quantities for each of the plurality of elements.

24. The determination device according to claim 23, wherein the processor is programmed to:
calculate a model representing the correlation between the respective element and the other respective element for each of the plurality of elements that are grouped.

25. The determination device according to claim 1, wherein
the first element is same as the third element.

26. The determination device according to claim 1, wherein:
the first correlation represents that an increase or a decrease in the extracted characteristic quantity of the first element causes an increase or a decrease in the extracted characteristic quantity of the second element; and
the second correlation represents that an increase or a decrease in the extracted characteristic quantity of the third element causes an increase or a decrease in the extracted characteristic quantity of the fourth element.

27. An analysis method for determining a correlation between a plurality of elements in a cell from a cell image, the cell image including an image of the cell to which a stimulus is applied, the plurality of elements in the cell including at least one of the cell and a substance that configures the cell, the method comprising:

causing a determination device to detect different regions in the cell image comprising a cell region, a nucleus region, a cytoplasm region, and a nuclear membrane region;

causing the determination device to extract changes in characteristic quantities for each of the plurality of elements in the cell from the cell image, the characteristic quantities comprising at least one or more statistics of luminance values in each of the cell region, the nucleus region, the cytoplasm region, and the nuclear membrane region;

causing the determination device to calculate a first correlation between a first element and a second element different from the first element among the plurality of elements in the cell, the first correlation being calculated based on a correlation between an extracted change in characteristic quantity of the first element and an extracted change in characteristic quantity of the second element;

causing the determination device to calculate a second correlation between a third element and a fourth element different from the third element among the plurality of elements in the cell, the second correlation being different from the first correlation and being calculated based on a correlation between an extracted change in characteristic quantity of the third element and an extracted change in characteristic quantity of the fourth element, each correlation being calculated as a cross-correlation between the extracted changes, each cross-correlation defining a strength of the correlation between the respective characteristic quantities;

causing the determination device to compare strength of the calculated first correlation with strength of the calculated second correlation to analyze the cell image; and causing the determination device to repeatedly analyze a new cell image until a model representing a correlation between a respective one of the plurality of elements and another respective one of the plurality of elements calculated by the determination device has a predetermined relationship.

28. The analysis method according to claim 27, wherein the cell image is an image captured while changing at least one of a time, a degree of change in a growth environment of the cell, and a degree of change in a state of the cell.

29. The analysis method according to claim 27, wherein the predetermined relationship is establishment of a directionality of at least a part of a relationship.

30. An analysis program stored on a non-transitory computer-readable medium for determining a correlation between a plurality of elements in a cell from a cell image, the cell image including an image of the cell to which a stimulus is applied, the plurality of elements in the cell including at least one of the cell and a substance that configures the cell, the analysis program comprising:

processing for causing a determination device to detect different regions in the cell image comprising a cell region, a nucleus region, a cytoplasm region, and a nuclear membrane region;

processing for causing the determination device to extract changes in characteristic quantities for each of the plurality of elements in the cell from the cell image, the characteristic quantities comprising at least one or more statistics of luminance values in each of the cell region, the nucleus region, the cytoplasm region, and the nuclear membrane region;

processing for causing the determination device to calculate a first correlation between a first element and a second element different from the first element among the plurality of elements in the cell, the first correlation being calculated based on a correlation between an extracted change in characteristic quantity of the first element and an extracted change in characteristic quantity of the second element;

processing for causing the determination device to calculate a second correlation between a third element and a fourth element different from the third element among the plurality of elements in the cell, the second correlation being different from the first correlation and being calculated based on a correlation between an extracted change in characteristic quantity of the third element and an extracted change in characteristic quantity of the fourth element, each correlation being calculated as a cross-correlation between the extracted changes, each cross-correlation defining a strength of the correlation between the respective characteristic quantities;

processing for causing the determination device to compare strength of the calculated first correlation with strength of the calculated second correlation to analyze the cell image; and processing for causing the determination device to repeatedly analyze a new cell image until a model representing a correlation between a respective one of the plurality of elements and another respective one of the plurality of elements calculated by the determination device has a predetermined relationship.

31. A cell manufacturing method using a determination device determining a correlation between a plurality of elements in a cell from a cell image, the cell image including an image of the cell to which a stimulus is applied, the plurality of elements in the cell including at least one of the cell and a substance that configures the cell, the method comprising:

a step of causing the determination device to detect different regions in the cell image comprising a cell region, a nucleus region, a cytoplasm region, and a nuclear membrane region;

a step of causing the determination device to extract changes in characteristic quantities for each of the plurality of elements in the cell from the cell image, the characteristic quantities comprising at least one or more statistics of luminance values in each of the cell region, the nucleus region, the cytoplasm region, and the nuclear membrane region;

a step of causing the determination device to calculate a first correlation between a first element and a second element different from the first element among the plurality of elements in the cell, the first correlation being calculated based on an extracted change in characteristic quantity of the first element and an extracted change in characteristic quantity of the second element;

a step of causing the determination device to calculate a second correlation between a third element and a fourth element different from the third element among the plurality of elements in the cell, the second correlation being different from the first correlation and being calculated based on a correlation between an extracted change in characteristic quantity of the third element and an extracted change in characteristic quantity of the fourth element, each correlation being calculated as a cross-correlation between the extracted changes, each cross-correlation defining a strength of the correlation between the respective characteristic quantities;

a step of causing the determination device to compare strength of the calculated first correlation with strength of the calculated second correlation to analyze the cell image; and a step of causing the determination device to repeatedly analyze a new cell image until a model representing a correlation between a respective one of the plurality of elements and another respective one of the plurality of elements calculated by the determination device has a predetermined relationship.

32. A cell manufactured using the cell manufacturing method according to claim 31.

\* \* \* \* \*